US012734208B2

(12) United States Patent
Campbell et al.

(10) Patent No.: US 12,734,208 B2
(45) Date of Patent: Sep. 15, 2026

(54) MODIFIED ANTIBODIES

(71) Applicant: Janux Therapeutics, Inc., San Diego, CA (US)

(72) Inventors: David Campbell, San Diego, CA (US); Ramesh Bhatt, San Diego, CA (US); William J. Dower, Menlo Park, CA (US); Steven E. Cwirla, Menlo Park, CA (US); Blake M. Williams, Menlo Park, CA (US)

(73) Assignee: JANUX THERAPEUTICS, INC., San Diego, CA (US)

( * ) Notice: Subject to any disclaimer, the term of this patent is extended or adjusted under 35 U.S.C. 154(b) by 951 days.

(21) Appl. No.: 18/063,419

(22) Filed: Dec. 8, 2022

(65) Prior Publication Data

US 2023/0270854 A1 Aug. 31, 2023

Related U.S. Application Data

(63) Continuation of application No. 15/988,944, filed on May 24, 2018, now abandoned.

(60) Provisional application No. 62/511,771, filed on May 26, 2017.

(51) Int. Cl.

| | |
|---|---|
| ***A61K 38/02*** | (2006.01) |
| ***A61K 39/00*** | (2006.01) |
| ***A61K 39/395*** | (2006.01) |
| ***A61P 35/00*** | (2006.01) |
| ***C07K 16/28*** | (2006.01) |

(52) U.S. Cl.

CPC ........ *A61K 38/02* (2013.01); *A61K 39/39558* (2013.01); *A61P 35/00* (2018.01); *C07K 16/2818* (2013.01); *C07K 16/2878* (2013.01); *A61K 2039/572* (2013.01); *A61K 2039/577* (2013.01); *A61K 2300/00* (2013.01); *C07K 2317/92* (2013.01); *C07K 2319/00* (2013.01)

(58) Field of Classification Search

CPC .............................. C07K 2/00; C07K 2317/92

See application file for complete search history.

(56) References Cited

U.S. PATENT DOCUMENTS

| | | | |
|---|---|---|---|
| 7,465,790 | B2 | 12/2008 | Waldmann et al. |
| 8,709,755 | B2 | 4/2014 | Short et al. |
| 8,859,467 | B2 | 10/2014 | Short |
| 9,683,985 | B2 | 6/2017 | Kodandapani et al. |
| 10,442,849 | B2 | 10/2019 | Baeuerle et al. |
| 2010/0158910 | A1 | 6/2010 | Law et al. |
| 2010/0260739 | A1 | 10/2010 | Short et al. |
| 2013/0028893 | A1 | 1/2013 | Waldmann et al. |
| 2013/0315906 | A1 | 11/2013 | Lowman et al. |
| 2015/0024944 | A1 | 1/2015 | Short |
| 2016/0129131 | A1 | 5/2016 | Vitari et al. |
| 2016/0144042 | A1 | 5/2016 | Williams et al. |
| 2016/0228546 | A1 | 8/2016 | Stagliano et al. |
| 2017/0191055 | A1 | 7/2017 | Short et al. |
| 2018/0339043 | A1 | 11/2018 | Campbell et al. |

FOREIGN PATENT DOCUMENTS

| | | | |
|---|---|---|---|
| WO | WO-2012033953 | A1 | 3/2012 |
| WO | WO-2013192546 | A1 | 12/2013 |
| WO | WO-2014004694 | A1 | 1/2014 |
| WO | WO-2014193973 | A2 | 12/2014 |
| WO | WO-2016004383 | A1 | 1/2016 |
| WO | WO-2016011210 | A2 | 1/2016 |
| WO | WO-2016036916 | A1 | 3/2016 |
| WO | WO-2016138071 | A1 | 9/2016 |
| WO | WO-2016149201 | A2 | 9/2016 |
| WO | WO-2016179003 | A1 | 11/2016 |
| WO | WO-2016200645 | A1 | 12/2016 |
| WO | WO-2017034615 | A1 | 3/2017 |
| WO | WO-2017075537 | A1 | 5/2017 |
| WO | WO-2018218076 | A1 | 11/2018 |

OTHER PUBLICATIONS

Chen and Han (Journal of Clinical Investigation, 2015, vol. 125, pp. 3384-3391) (Year: 2015).*

Barar and Omidi (BioImpacts, 2013, vol. 3, pp. 149-162) (Year: 2013).*

Castaneda et al. Acid-cleavable thiomaleamic acid linker for homogeneous antibody-drug conjugation, Chem. Commun. 49:8187-8189 (2013).

Grant et al. Matrigel induces thymosin h 4 gene in differentiating endothelial cells. J Cell Sci 108:3685-3694 (1995).

Le Gall et al. Immunosuppressive properties of anti-CD3 single-chain Fv and diabody. J Immunol Methods 285(1):111-127 (2004).

Murtaugh et al. A combinatorial histidine scanning library approach to engineer highly pH-dependent protein switches. Protein Sci 20(9):1619-1631 (2011).

PCT/US2018/034480 International Search Report and Written Opinion dated Oct. 1, 2018.

PCT/US2018/034480 Invitation to Pay Additional Fees dated Aug. 6, 2018.

Takeuchi et al. Roles of the histidine and tryptophan side chains in the M2 proton channel from influenza A virus. FEBS Lett 552(1):35-38 (2003).

U.S. Appl. No. 15/988,944 Office Action dated Feb. 16, 2022.

U.S. Appl. No. 15/988,944 Office Action dated Mar. 9, 2021.

U.S. Appl. No. 15/988,944 Office Action dated Sep. 13, 2021.

U.S. Appl. No. 15/988,944 Office Action dated Sep. 9, 2022.

Zhong et al. Cathepsin B-cleavable doxorubicin prodrugs for targeted cancer therapy (Review). Int J Oncol 42(2):373-83 (2013).

* cited by examiner

*Primary Examiner* — Karen A. Canella

(74) *Attorney, Agent, or Firm* — WILSON SONSINI GOODRICH & ROSATI

(57) ABSTRACT

Provided herein are modified antibodies, pharmaceutical compositions thereof, as well as nucleic acids, and methods for making and discovering the same. The modified antibodies described herein are modified with a peptide. The peptide binds at or near the antigen binding site of the antibody at physiological pH, thus reducing binding affinity of the antibody for a target antigen. At acidic pH, the binding interaction of the peptide at or near the antigen binding site is disrupted, thus enabling binding with a target antigen.

19 Claims, 16 Drawing Sheets

Specification includes a Sequence Listing.

MODIFIED ANTIBODIES

CROSS-REFERENCE

This application is a continuation of U.S. patent application Ser. No. 15/988,944, filed May 24, 2018, which claims the benefit of U.S. Provisional Application No. 62/511,771 filed May 26, 2017 which is incorporated by reference herein in its entirety.

REFERENCE TO A SEQUENCE LISTING

The instant application contains a Sequence Listing which has been submitted electronically in XML format and is hereby incorporated by reference in its entirety. Said XML copy, created on May 15, 2023, is named 52426-701301.xml and is 152,187 bytes in size.

SUMMARY OF THE INVENTION

Disclosed herein, in some embodiments, are modified antibodies comprising a formula: A-L-P wherein A is an antibody or antibody fragment that binds to a target antigen, P is a peptide that reduces binding of A to the target antigen at physiological pH and that does not reduce binding of A to the target antigen at acidic pH, and L is a linking moiety that connects A to P at physiological pH and in a tumor microenvironment and L is bound to A outside an antigen binding site. In some instances, at physiological pH P is reversibly bound to A through ionic, electrostatic, hydrophobic, Pi-stacking, and H-bonding interactions, or a combination thereof. In some instances, at physiological pH P is reversibly bound to A at or near the antigen binding site. In some instances, P inhibits the binding of A to the target antigen at physiological pH and P does not inhibit the binding of A to the target antigen at acidic pH. In some instances, in tissue other than the tumor microenvironment, P sterically blocks A from binding to the target antigen. In some instances, at the tumor microenvironment, P is removed from the antigen binding site, and the antigen binding site of A is exposed. In some instances, the modified antibody has an increased binding affinity for the target antigen in the tumor microenvironment compared to the binding affinity of the modified antibody for the target antigen in a non-tumor microenvironment. In some instances, P comprises a peptide sequence with at least one histidine. In some instances, the histidine forms a binding interaction at or near the antigen binding site of A at physiological pH. In some instances, at acidic pH P is reversibly bound to A in a region of A that is not the antigen binding site. In some instances, at acidic pH P is reversibly bound to A in a region of A that is not the antigen binding site through ionic, electrostatic, hydrophobic, Pi-stacking and H-bonding interactions, or a combination thereof. In some instances, P is resistant to cleavage by a protease. In some instances, physiological pH is about pH 7.4. In some instances, acidic pH is about pH 6.0 to about pH 7.0. In some instances, P comprises a peptide sequence of at least 6 amino acids in length. In some instances, P comprises a peptide sequence of at least 10 amino acids in length. In some instances, P comprises a peptide sequence of at least 6 to 20 amino acids in length. In some instances, P comprises a modified amino acid, a non-natural amino acid, or a modified non-natural amino acids, or combination thereof. In some instances, the modified amino acid or modified non-natural amino acid comprises a post-translational modification. In some instances, at acidic pH P is reversibly bound to L. In some instances, L comprises a peptide sequence with at least one aspartic acid or glutamic acid, or a combination thereof. In some instances, the histidine of P forms an interaction with the aspartic acid or glutamic acid of L. In some instances, L is a peptide sequence having at least 5 to no more than 50 amino acids. In some instances, L has a formula selected from the group consisting of: $(GS)_n$, wherein n is an integer from 6 to 20 (SEQ ID NO: 1); $(G_2S)_n$, wherein n is an integer from 4 to 13 (SEQ ID NO: 2); $(G_3S)_n$, wherein n is an integer from 3 to 10 (SEQ ID NO: 3); and $(G_4S)_n$, wherein n is an integer from 2 to 8 (SEQ ID NO: 4); and $(G)_n$, wherein n is an integer from 12 to 40 (SEQ ID NO: 5). In some instances, L has a formula comprising $(GGSGGD)_n$, wherein n is an integer from 2 to 6 (SEQ ID NO: 8). In some instances, L has a formula comprising $(GGSGGE)_n$, wherein n is an integer from 2 to 6 (SEQ ID NO: 9). In some instances, L has a formula comprising $(GGGSGSGGGGS)_n$, wherein n is an integer from 1 to 3 (SEQ ID NO: 6). In some instances, L has a formula comprising $(GGGGGPGGGGP)_n$, wherein n is an integer from 1 to 3 (SEQ ID NO: 7). In some instances, L has a formula selected from $(GX)_n$, wherein X is serine, aspartic acid, glutamic acid, threonine, or proline and n is at least 20 (SEQ ID NO: 24); $(GGX)_n$, wherein X is serine, aspartic acid, glutamic acid, threonine, or proline and n is at least 13 (SEQ ID NO: 25); $(GGGX)_n$, wherein X is serine, aspartic acid, glutamic acid, threonine, or proline and n is at least 10 (SEQ ID NO: 26); $(GGGGX)_n$, wherein X is serine, aspartic acid, glutamic acid, threonine, or proline and n is at least 8 (SEQ ID NO: 27); $(G_zX)_n$, wherein X is serine, aspartic acid, glutamic acid, threonine, or proline and n is at least 15, and z is between 1 and 20 (SEQ ID NO: 28). In some instances, L is resistant to cleavage by a protease. In some instances, L comprises a modified amino acid. In some instances, the modified amino acid comprises a post-translational modification. In some instances, L comprises a non-natural amino acid or a modified non-natural amino acid, or combination thereof. In some instances, the modified non-natural amino acid comprises a post-translational modification. In some instances, the target antigen is selected from the group consisting of: 4-1BB, CTLA4, PD-1, and PD-L1. In some instances, the target antigen is 4-1BB. In some instances, the target antigen is CTLA4. In some instances, the target antigen is PD-1. In some instances, the target antigen is PD-L1. In some instances, A is a full length antibody, a single-chain antibody, an Fab fragment, an Fab' fragment, an (Fab')2 fragment, an Fv fragment, a divalent single chain antibody, bispecific antibody, a trispecific antibody, a tetraspecific antibody, or an antibody drug conjugate. In some instances, A is selected from the group consisting of utomilumab, urelumab, ipilimumab, tremelimumab, pembrolizumab, nivolumab, and atezolizumab. In some instances, A is utomilumab. In some instances, A is urelumab. In some instances, A is ipilimumab. In some instances, A is tremelimumab. In some instances, A is pembrolizumab. In some instances, A is nivolumab. In some instances, A is atezolizumab. In some instances, P comprises an amino acid sequence selected from the group consisting of Peptide 1, Peptide 2, Peptide 5, Peptide 6, Peptide 10, Peptide 13, Peptide 26, Peptide 14, Peptide 15, Peptide 20, Peptide 27, Peptide 21, Peptide 22, Peptide 23, Peptide 28, Peptide 29, Peptide 30, Peptide 31, and Peptide 24. In some instances, the target antigen is CTLA4 and P comprises an amino acid sequence selected from the group consisting of Peptide 1, Peptide 2, Peptide 5, Peptide 6, Peptide 10, Peptide 13, Peptide 26, Peptide 14, and Peptide 15. In some instances, the target antigen is CTLA4 and P comprises an amino acid sequence according to Peptide 1. In some instances, the target antigen is CTLA4 and P comprises an amino acid sequence according to Peptide 2. In some instances, the target antigen is CTLA4 and P comprises an amino acid sequence according to Peptide 5. In some instances, the target antigen is CTLA4 and P comprises an amino acid sequence according to Peptide 6. In some instances, the target antigen is CTLA4 and P comprises an amino acid sequence according to Peptide 10. In some instances, the target antigen is CTLA4 and P comprises an amino acid sequence according to Peptide 13. In some instances, the target antigen is CTLA4 and P comprises an amino acid sequence according to Peptide 26. In some instances, the target antigen is CTLA4 and P comprises an amino acid sequence according to Peptide 14. In some instances, the target antigen is CTLA4 and P comprises an amino acid sequence according to Peptide 15. In some instances, the target antigen is CTLA4 and P comprises an amino acid sequence selected from the group consisting of Peptide 10, Peptide 13, Peptide 26, Peptide 14, and Peptide 15. In some instances, the target antigen is PD-L1 and P comprises an amino acid sequence selected from the group consisting of Peptide 20, Peptide 27, Peptide 21, Peptide 22, Peptide 23, Peptide 28, Peptide 29, Peptide 30, Peptide 31, and Peptide 24. In some instances, the target antigen is PD-L1 and P comprises an amino acid sequence according to Peptide 20. In some instances, the target antigen is PD-L1 and P comprises an amino acid sequence according to Peptide 27. In some instances, the target antigen is PD-L1 and P comprises an amino acid sequence according to Peptide 21. In some instances, the target antigen is PD-L1 and P comprises an amino acid sequence according to Peptide 22. In some instances, the target antigen is PD-L1 and P comprises an amino acid sequence according to Peptide 23. In some instances, the target antigen is PD-L1 and P comprises an amino acid sequence according to Peptide 28. In some instances, the target antigen is PD-L1 and P comprises an amino acid sequence according to Peptide 29. In some instances, the target antigen is PD-L1 and P comprises an amino acid sequence according to Peptide 30. In some instances, the target antigen is PD-L1 and P comprises an amino acid sequence according to Peptide 31. In some instances, the target antigen is PD-L1 and P comprises an amino acid sequence according to Peptide 24. In some instances, the target antigen is PD-L1 and P comprises an amino acid sequence selected from the group consisting of Peptide 27, Peptide 22, Peptide 23, and Peptide 31. In some instances, A comprises a kappa light chain amino acid sequence according to SEQ ID NO: 68. In some instances, A comprises a heavy chain amino acid sequence according to SEQ ID NO: 70. In some instances, the modified antibody comprises an amino acid sequence according to SEQ ID NO: 69. In some instances, P comprises an amino acid sequence selected from the group consisting of Peptide 1, Peptide 2, Peptide 5, Peptide 6, Peptide 10, Peptide 13, Peptide 26, Peptide 14, Peptide 15, Peptide 20, Peptide 21, Peptide 22, Peptide 23, Peptide 31, and Peptide 24. In some instances, P comprises a peptide sequence with at least two histidines. In some instances, P comprises an amino acid sequence selected from the group consisting of Peptide 5, Peptide 13, Peptide 26, Peptide 14, Peptide 15, Peptide 31, and Peptide 24. In some instances, P comprises a peptide sequence with at least two histidines and at least two cysteines. In some instances, P comprises a peptide sequence with at least two charged amino acid residues wherein the charged amino acid residues are selected from the group consisting of aspartate, glutamate, and histidine. In some instances, P comprises an amino acid sequence selected from the group consisting of Peptide 1, Peptide 2, Peptide 5, Peptide 6, Peptide 10, Peptide 13, Peptide 26, Peptide 14, Peptide 15, Peptide 20, Peptide 27, Peptide 21, Peptide 22, Peptide 23, Peptide 28, Peptide 29, Peptide 30, Peptide 31, and Peptide 24. In some instances, P comprises a peptide sequence with at least three charged amino acid residues wherein the charged amino acid residues are selected from the group consisting of aspartate, glutamate, and histidine. In some instances, P comprises an amino acid sequence selected from the group consisting of Peptide 1, Peptide 2, Peptide 5, Peptide 10, Peptide 13, Peptide 26, Peptide 14, Peptide 15, Peptide 21, Peptide 23, Peptide 28, Peptide 31, and Peptide 24. In some instances, P comprises a peptide sequence with at least one histidine and at least two aspartates. In some instances, P comprises a peptide sequence with at least one cysteine. In some instances, P comprises an amino acid sequence selected from the group consisting of Peptide 5, Peptide 6, Peptide 10, Peptide 13, Peptide 26, Peptide 14, Peptide 15, Peptide 22, Peptide 23, Peptide 29, Peptide 30, Peptide 31, and Peptide 24. In some instances, P comprises a peptide sequence with at least two cysteine amino acid residues. In some instances, P comprises an amino acid sequence selected from the group consisting of Peptide 6, Peptide 10, Peptide 13, Peptide 26, Peptide 14, Peptide 22, Peptide 23, Peptide 29, Peptide 30, Peptide 31, and Peptide 24. In some instances, P comprises a peptide sequence with at least two cysteines and at least three charged amino acid residues wherein the charged amino acid residues are selected from the group consisting of aspartate, glutamate, and histidine. In some instances, P comprises an amino acid sequence of formula GGX, wherein X is cysteine, alanine, proline, methionine, histidine, or leucine. In some instances, P comprises an amino acid sequence selected from the group consisting of Peptide 5, Peptide 6, Peptide 10, Peptide 13, Peptide 26, Peptide 14, Peptide 15, Peptide 22, Peptide 23, Peptide 29, Peptide 31, and Peptide 24. In some instances, P comprises an amino acid sequence of GGC. In some instances, P comprises an amino acid sequence selected from the group consisting of Peptide 5, Peptide 6, Peptide 13, Peptide 26, Peptide 14, Peptide 31, and Peptide 24. In some instances, P does not comprise a lysine or arginine. In some instances, P comprises at least one histidine and at least one aspartate. In some instances, P comprises at least one histidine and at least one glutamate. In some instances, P comprises at least one histidine and at least two glutamates. In some instances, P comprises at least two histidines and at least one aspartate or at least one glutamate. In some instances, P comprises at least one histidine, wherein at least one hydrogen bonding amino acid residue is within two amino acid positions to the histidine, wherein the hydrogen bonding amino acid residue is selected from the group consisting of serine, threonine, tyrosine, asparagine, and glutamine. In some instances, the hydrogen bonding amino acid residue is within one amino acid position to the histidine. In some instances, the hydrogen bonding amino acid residue is serine. In some instances, the hydrogen bonding amino acid residue is threonine. In some instances, the hydrogen bonding amino acid residue is tyrosine. In some instances, the hydrogen bonding amino acid residue is asparagine. In some instances, the hydrogen bonding amino acid residue is glutamine. In some instances, A-L-P does not comprise a protease cleavage site that releases A from P in a tumor microenvironment. In some instances, L comprises a peptide sequence with at least one histidine. In some instances, at acidic pH L is reversibly bound to P. In some instances, P comprises a peptide sequence with at least one aspartic acid or glutamic acid, or a combination thereof. In some instances, the histidine of L forms an interaction with the aspartic acid or glutamic acid of P.

Disclosed herein, in some embodiments, are pharmaceutical compositions, comprising: (a) a modified antibody according to any of the disclosures herein; and (b) a pharmaceutically acceptable excipient.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A illustrates peptide candidates identified that exhibit pH dependent binding to anti-CTLA4. FIG. 10B illustrates peptide candidates identified that exhibit pH dependent dissociation to anti-CTLA4.

DETAILED DESCRIPTION OF THE INVENTION

Figure 1:
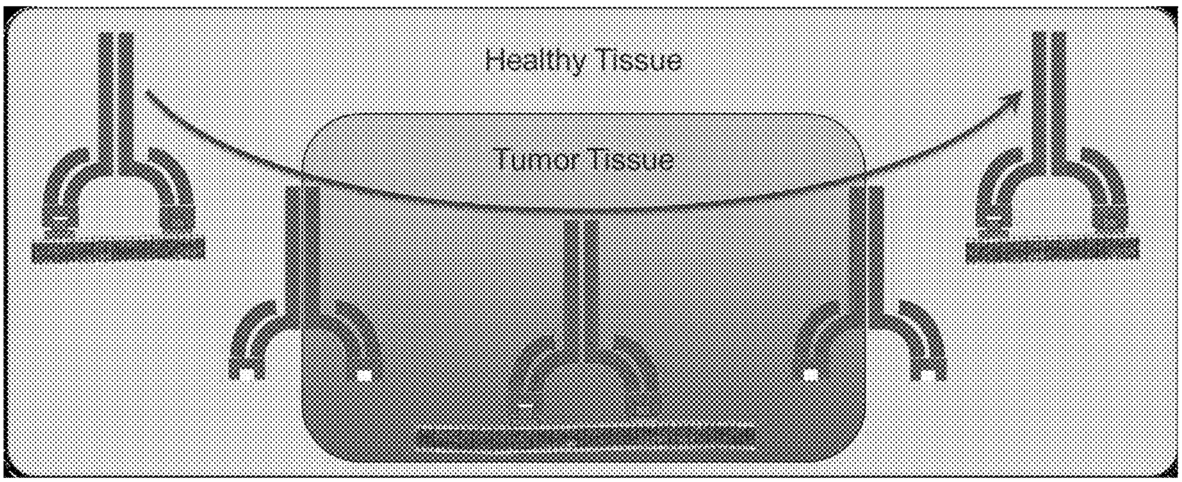
FIG. 1 exemplifies an antibody that does not comprise a peptide modification. Such antibodies bind to unique antigens that exist in abundance in tumor tissue. But, the unique antigens are also found in some healthy tissues, which can trigger systemic immune activation in a subject, and cause toxicity.
Figure 2:
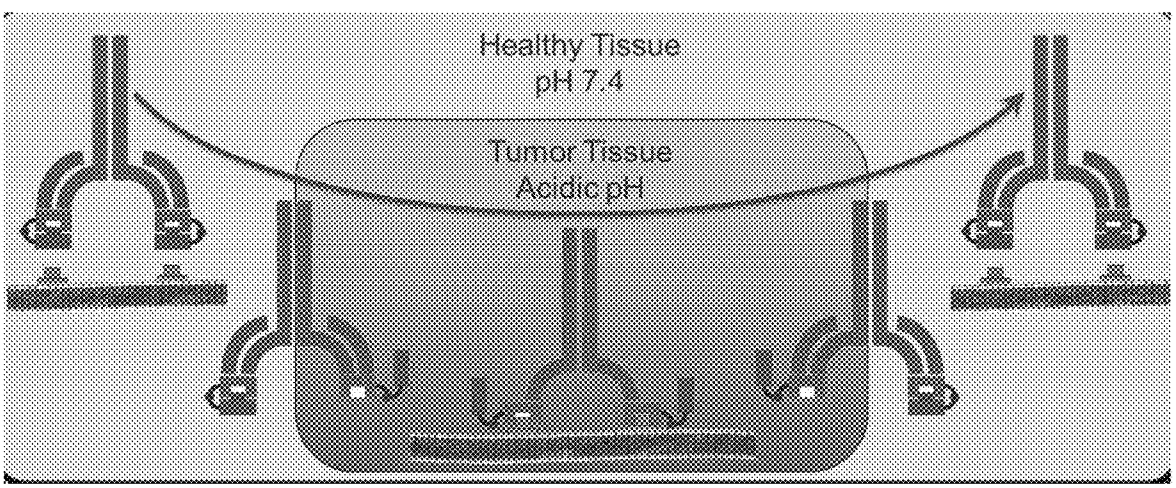
FIG. 2 shows an exemplary modified antibody. In this example, the modified antibody is linked to a peptide which binds at or near the antigen binding site of the modified antibody at pH 7.4. This reduces binding of the modified antibody to its target antigen in healthy tissue. In tumor tissue, the acidic tumor microenvironment disrupts the interaction of the peptide with the modified antibody. The antigen binding site of the modified antibody is exposed, and the modified antibody selectively binds to its target antigen in tumor tissue.
Figure 3:
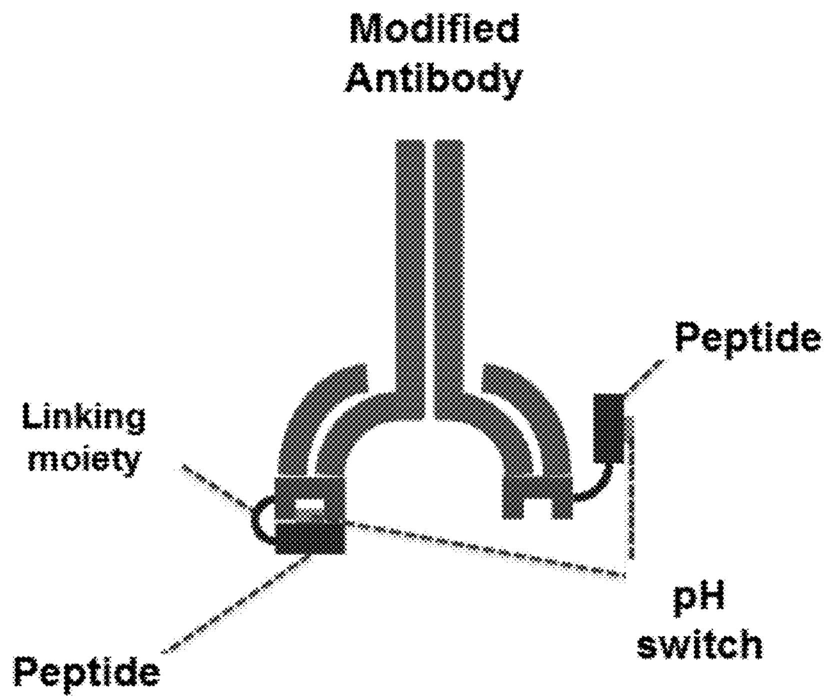
FIG. 3 shows an exemplary modified antibody. The peptide is linked to the antibody via a linking moiety. The linking moiety creates a stable link between the antibody and peptide. The peptide prevents the antibody from binding to its target antigen in physiological pH, non-diseased tissue. A pH switch in tumor microenvironments modulates the peptide/antibody affinity. The peptide is released in tumor tissue, and enables the antibody to bind to its target antigen.
Figure 4:
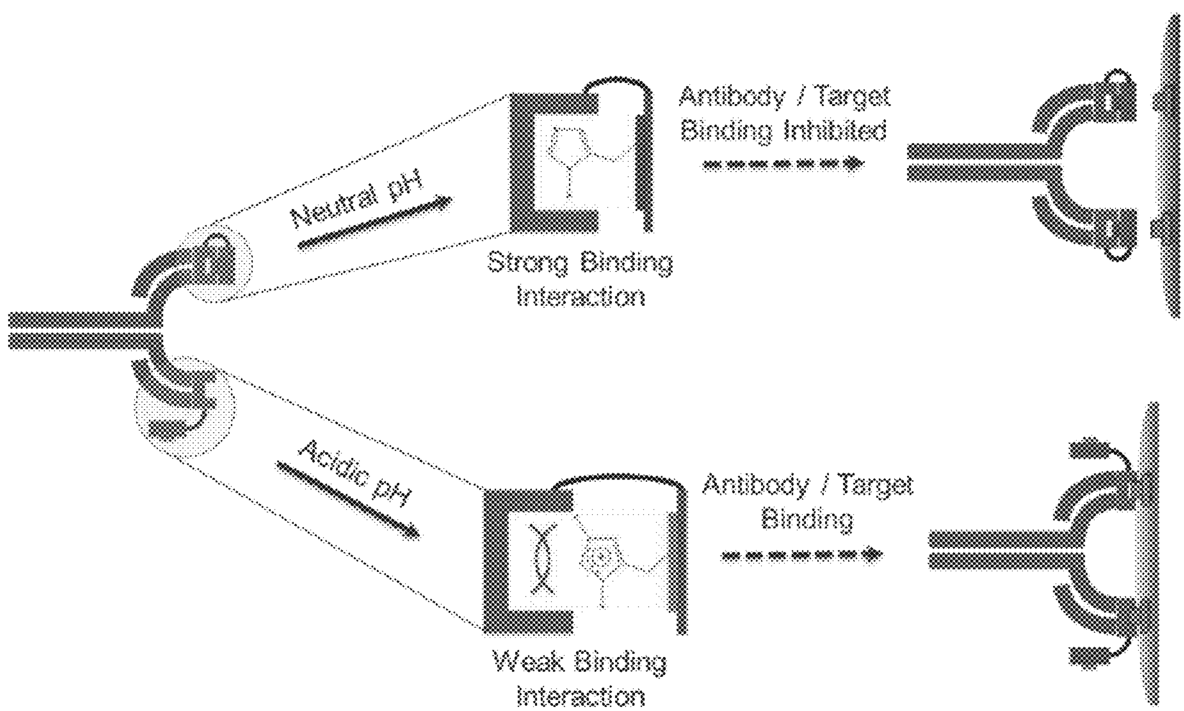
FIG. 4 shows an exemplary modified antibody. In this example, the peptide is engineered to contain a histidine. At physiological pH, the histidine of the peptide interacts with the antibody binding site. At acidic pH, such as in a tumor microenvironment, the interaction between the peptide and the antibody binding site is disfavored because the histidine is protonated. The antibody binding site is available for binding to its target antigen in a tumor microenvironment.
Figure 5:
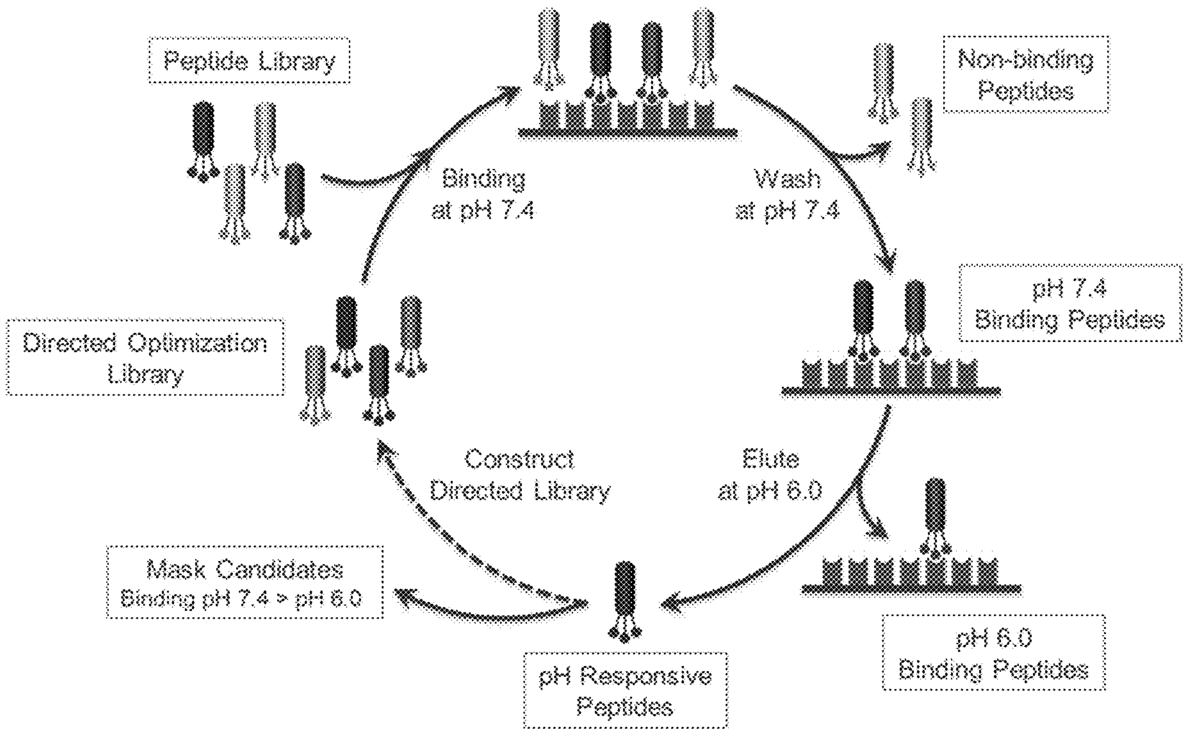
FIG. 5 is an exemplary schematic of phage panning screening platform to identify pH responsive peptide candidates.
Figure 6:
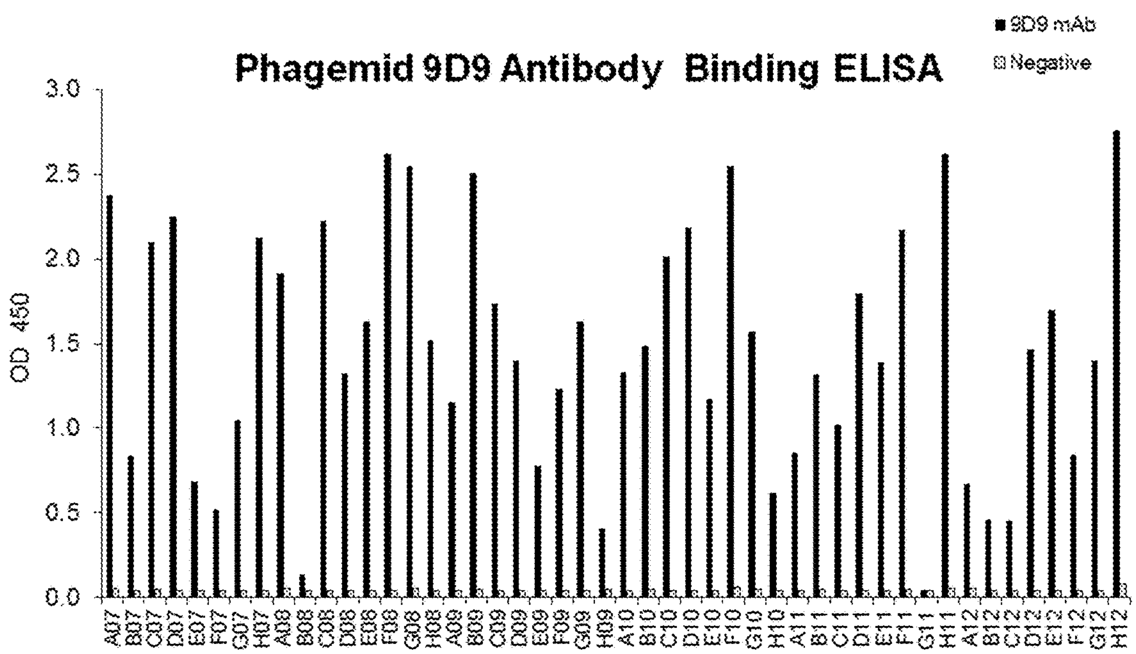
FIG. 6 illustrates a phagemid ELISA of a collection of enriched clones resulting from three rounds of biopanning against anti-mouse CTLA-4 (clone 9D9).
Figure 7:
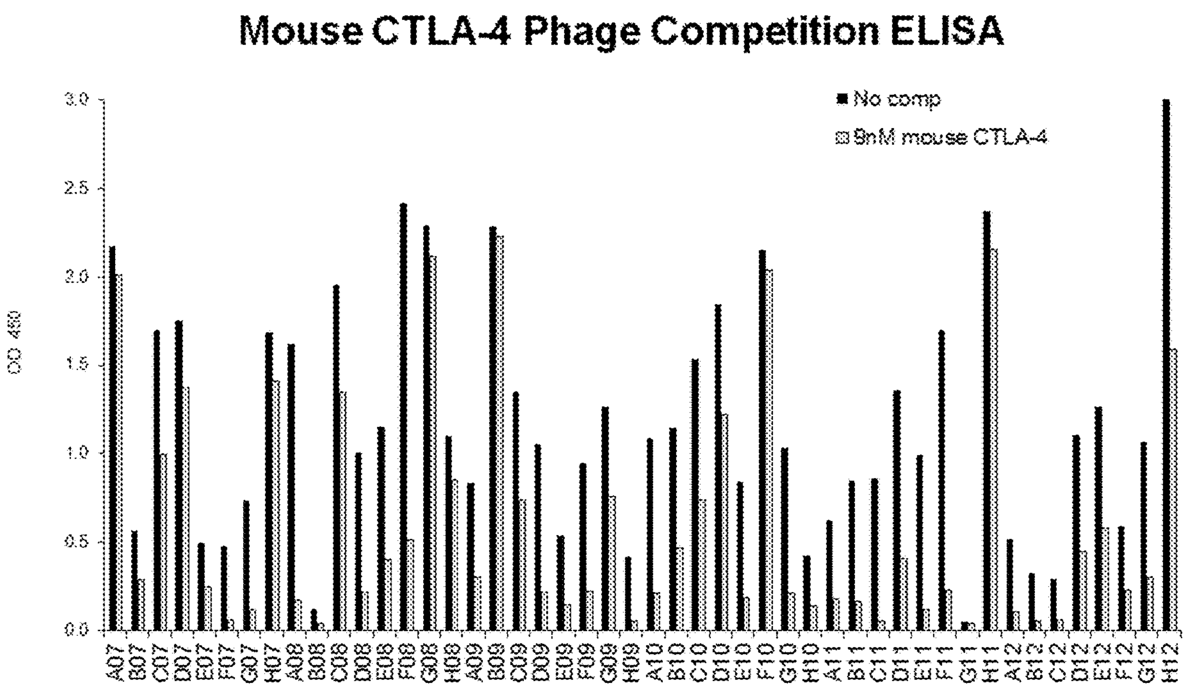
FIG. 7 is an exemplary phagemid competition ELISA from a collection of enriched clones isolated after three rounds of biopanning against anti-mouse CTLA-4 (clone 9D9).
Figure 8:
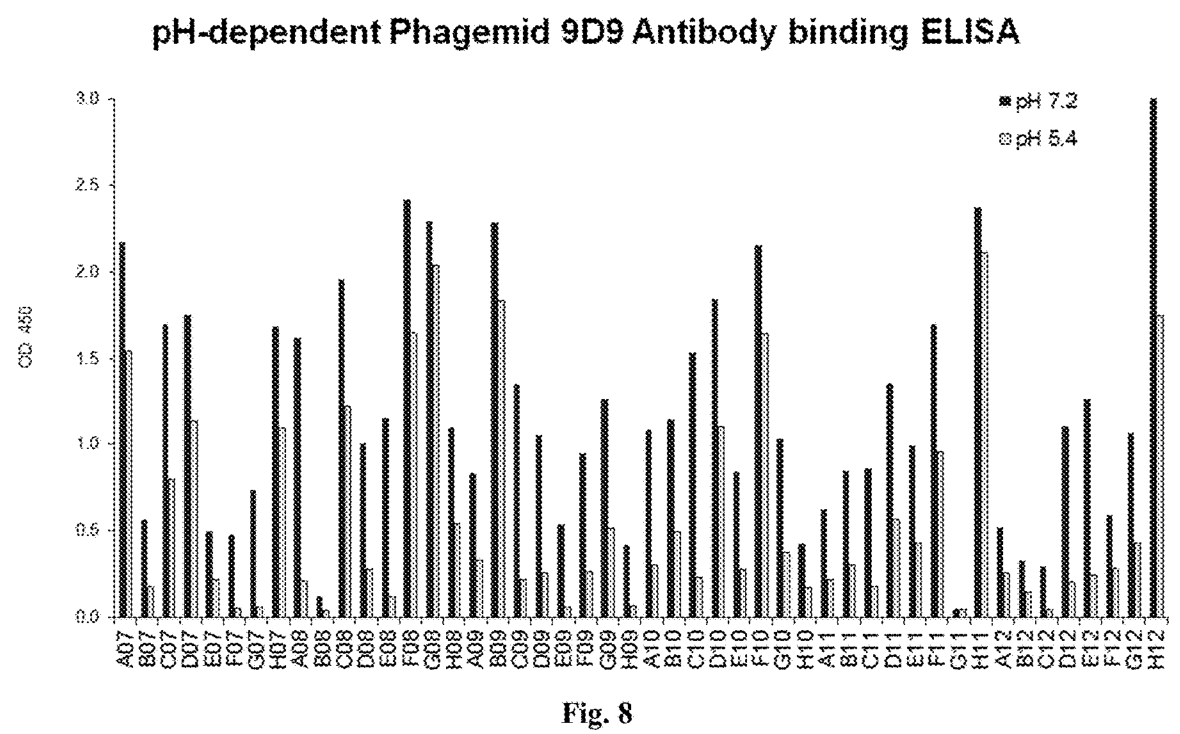
FIG. 8 is an exemplary pH-dependent "binding" assay of a collection of enriched clones isolated after three rounds of biopanning against anti-mouse CTLA-4 (clone 9D9).
Figure 9:
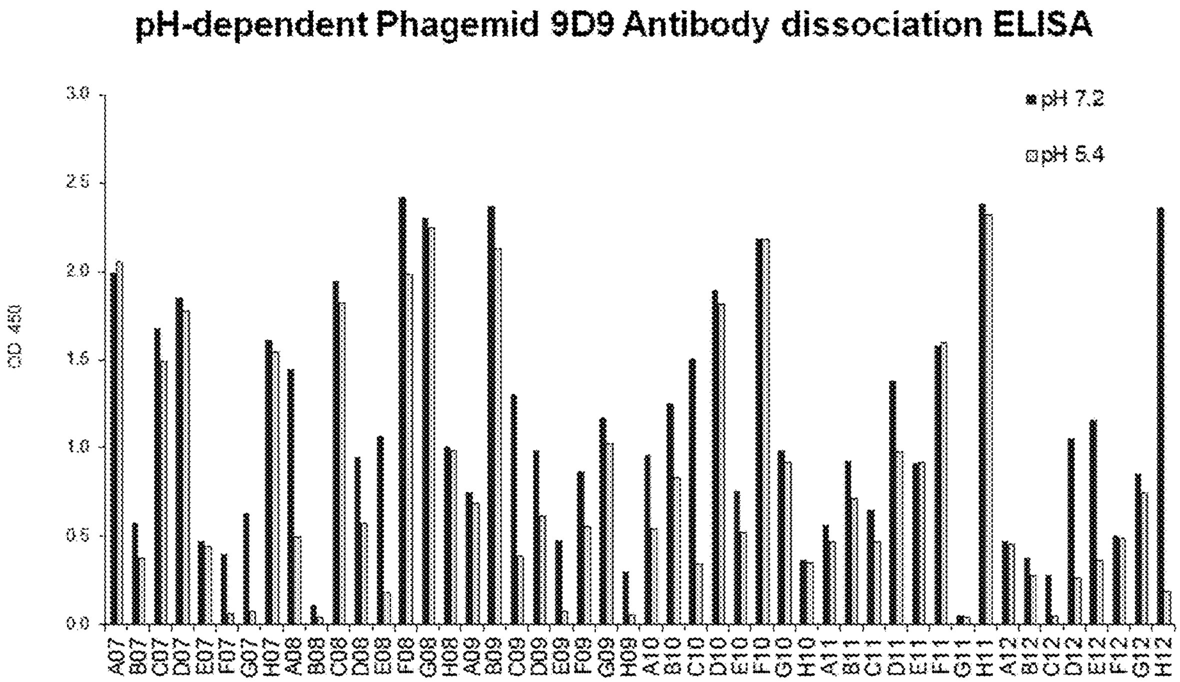
FIG. 9 illustrates a pH-dependent "dissociation" assay of a collection of enriched clones isolated after three rounds of biopanning against anti-mouse CTLA-4 (clone 9D9).
Figure 10A:
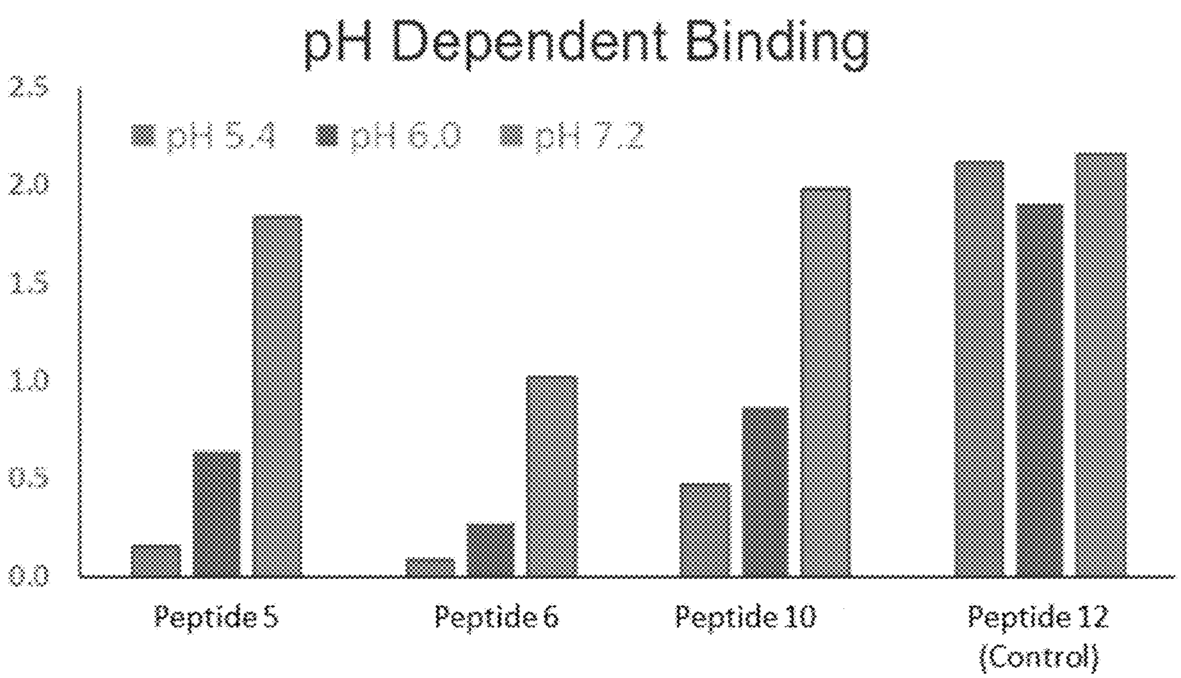
FIG. 10A-FIG. 10B illustrate pH responsive anti-CTLA4 peptide candidates identified with phage panning screening platform
Figure 10B:
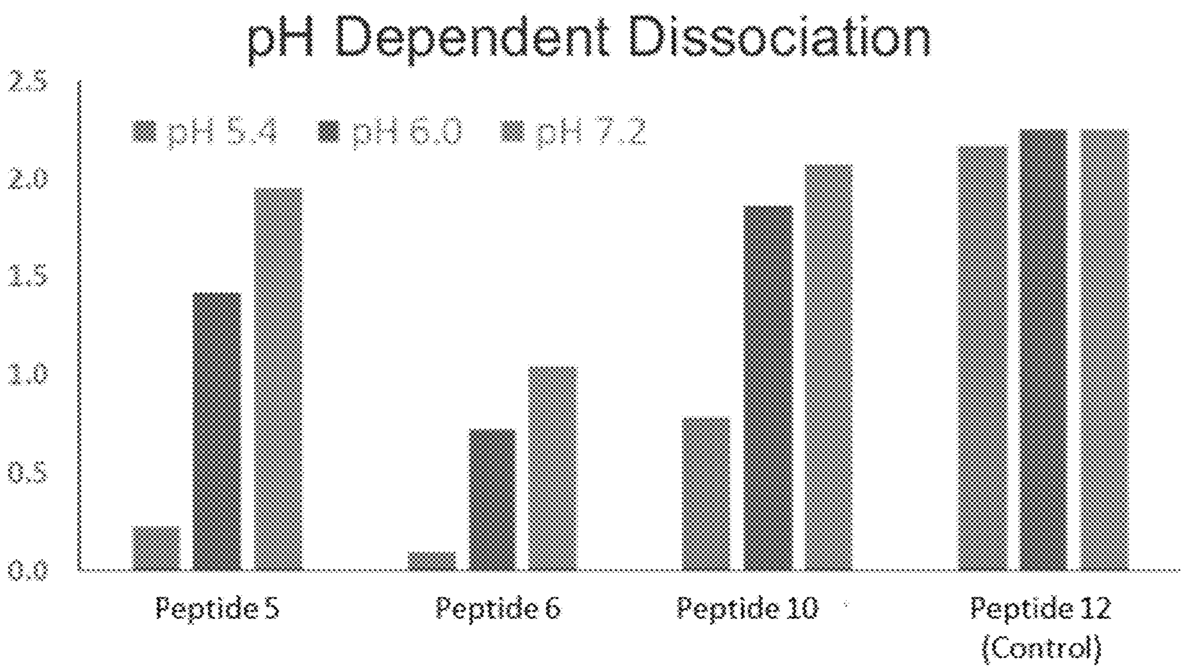
Figure 11A:
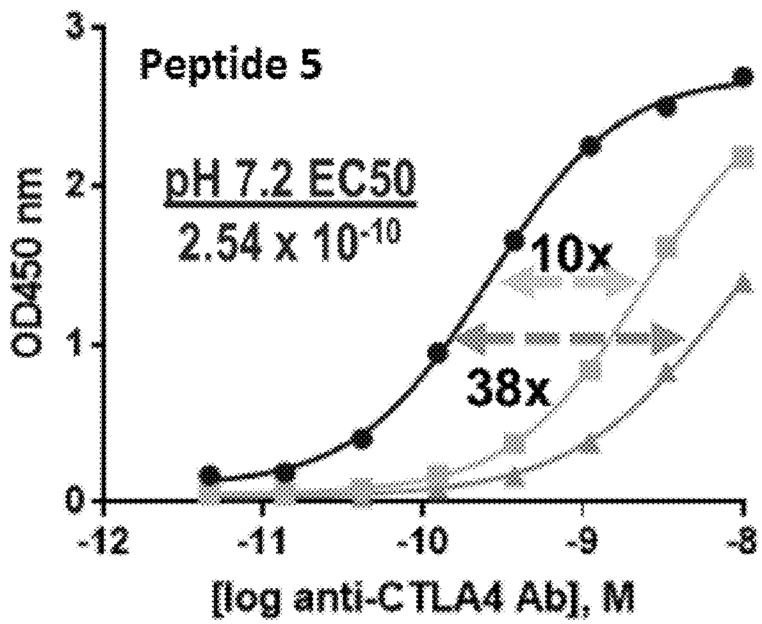
FIG. 11A-FIG. 11C illustrate significant pH responsiveness of unoptimized peptide candidates Peptide 5 (FIG. 11A), Peptide 6 (FIG. 11B) and Peptide 10 (FIG. 11C).
Figure 11B:
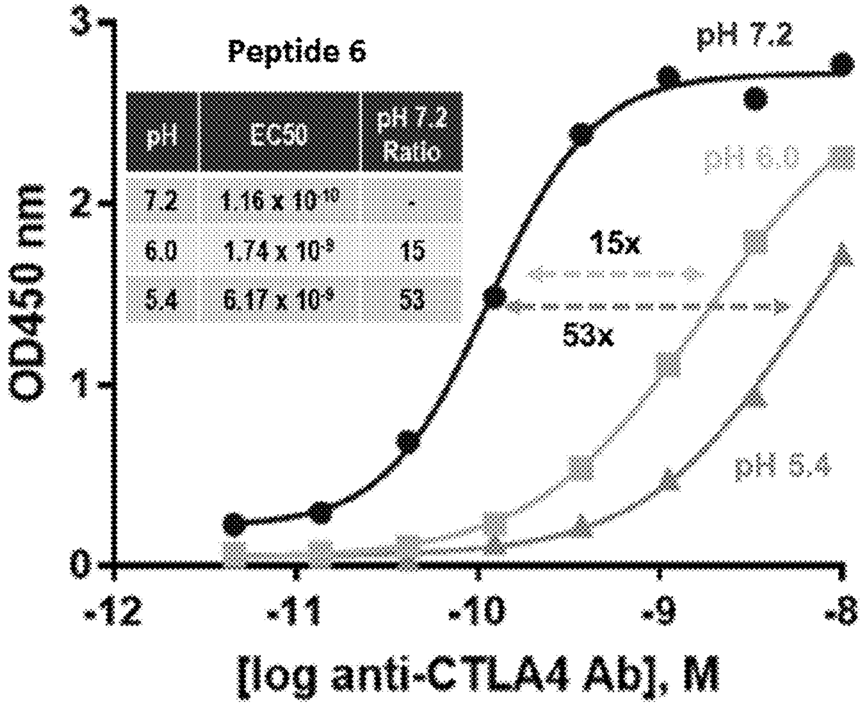
Figure 11C:
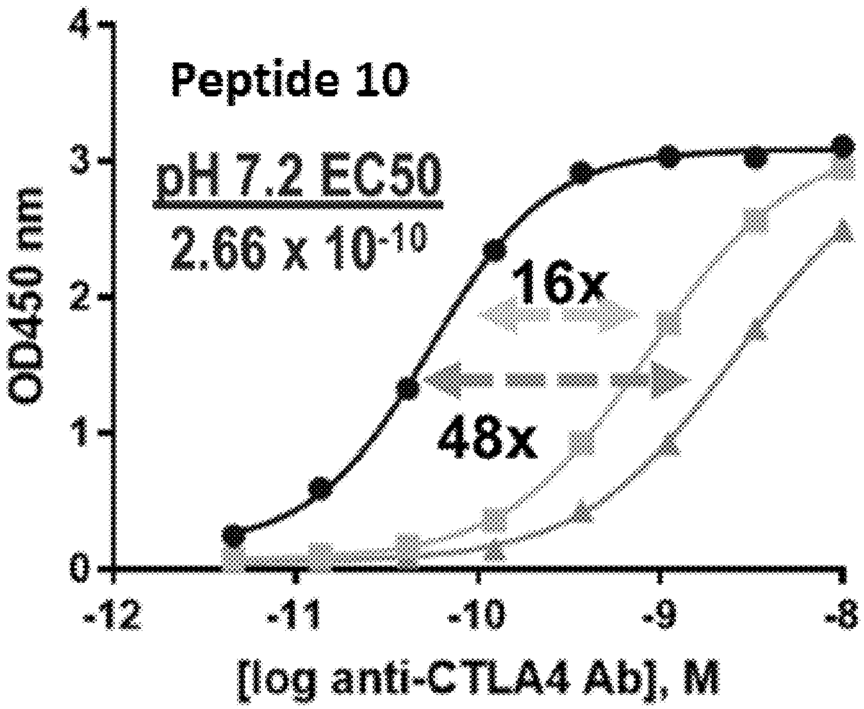
Figure 12:
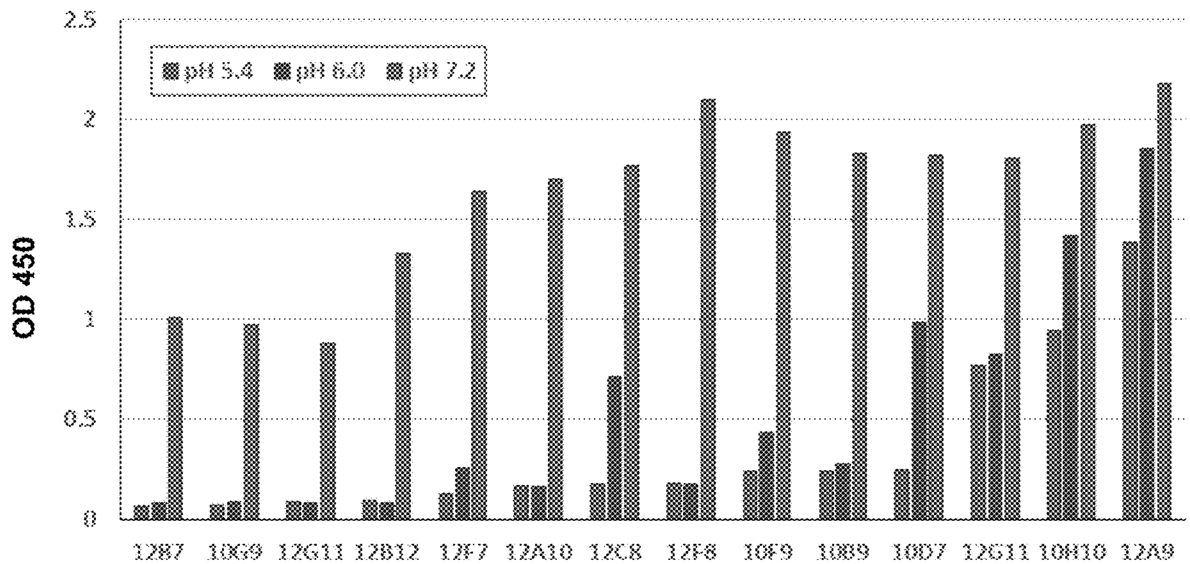
FIG. 12 illustrates multiple pH response anti-CTLA4 peptide candidates with pH dependent dissociation identified from biased library.
Figure 13A:
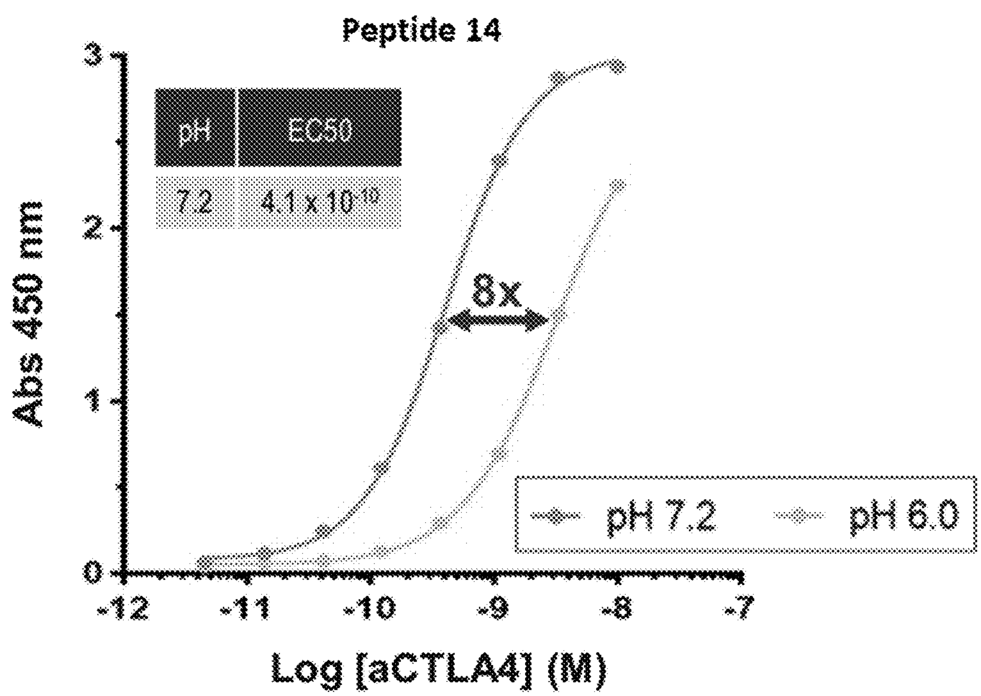
FIG. 13A-FIG. 13B illustrate pH biased library generated peptide candidates Peptide 14 (FIG. 13A) and Peptide 15 (FIG. 13B).
Figure 13B:
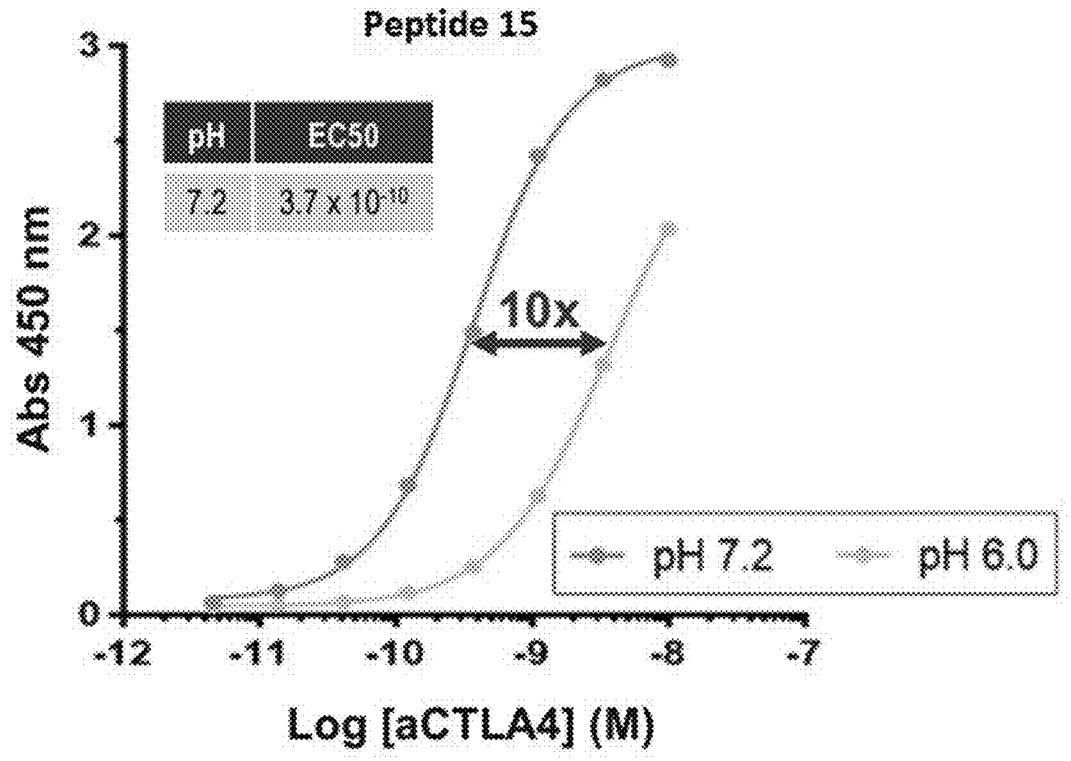
Figure 14:
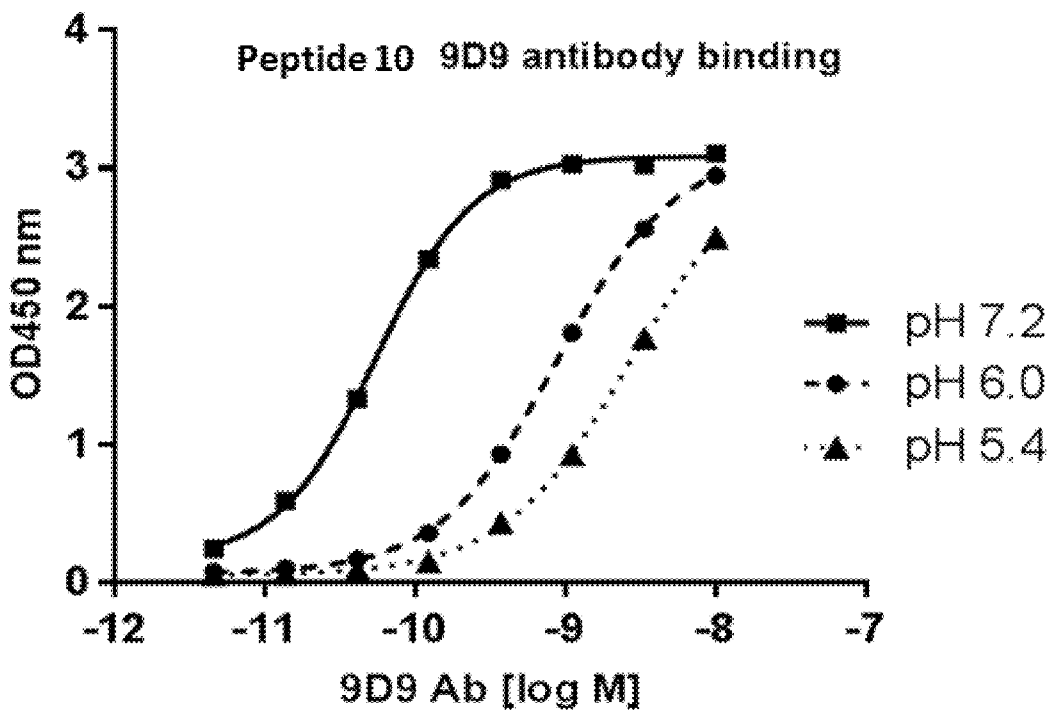
FIG. 14 illustrates a Peptide 10 ELISA to anti-mouse antibody (clone 9D9).
Figure 15:
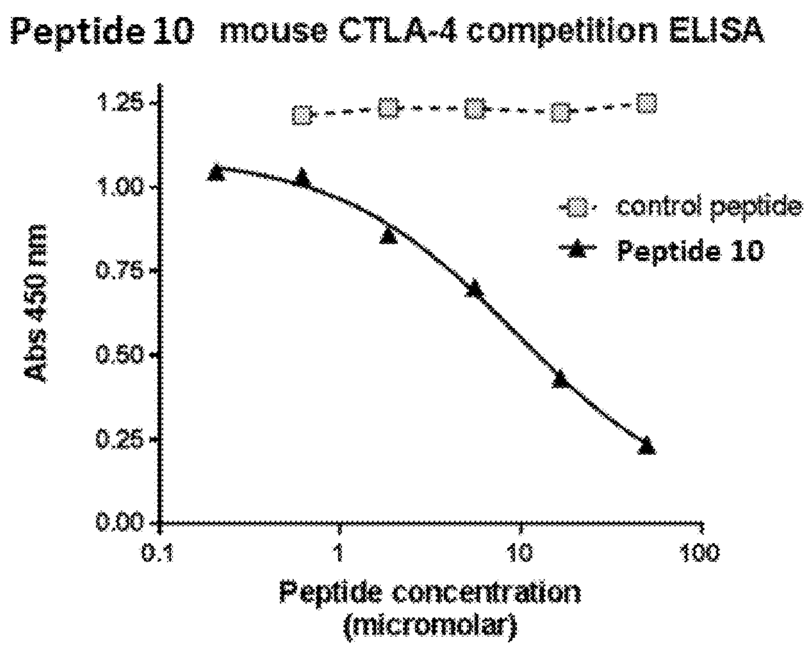
FIG. 15 illustrates a Peptide 10 competition ELISA.
Figure 16A:
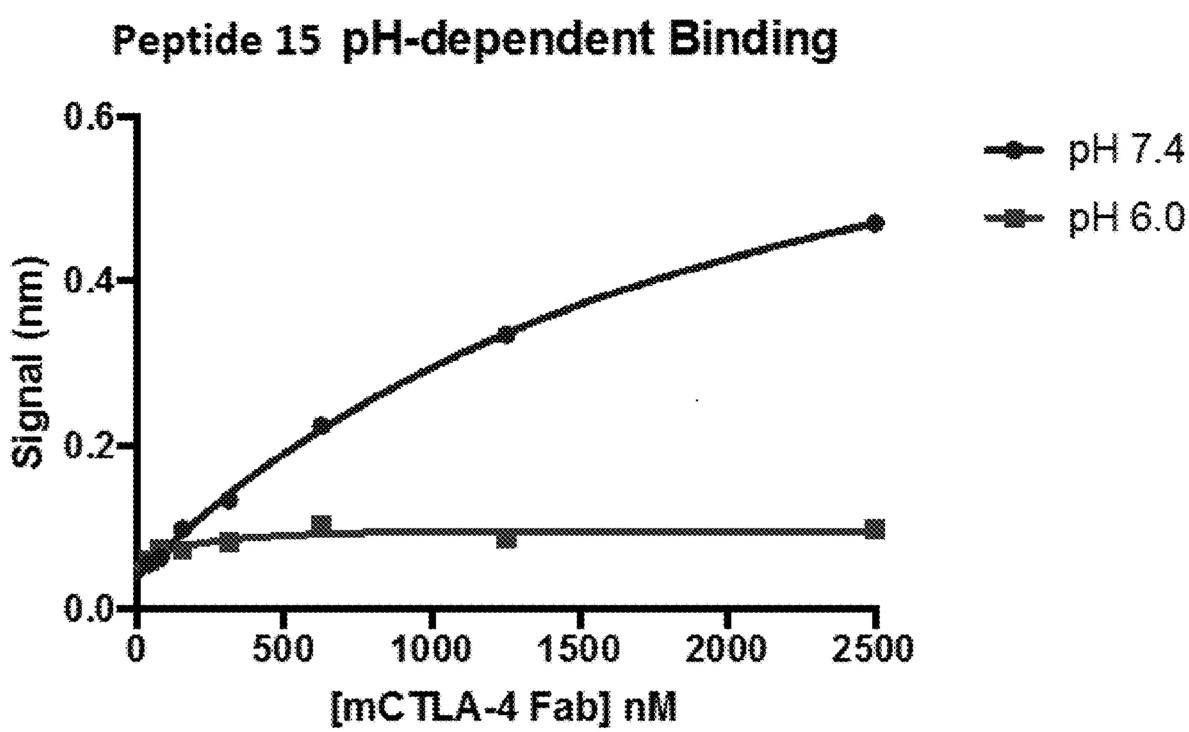
FIG. 16A-FIG. 16C illustrate octet binding curve of Peptide 15 (FIG. 16A), Peptide 17 (FIG. 16C) and Peptide 18 (FIG. 16C).
Figure 16B:
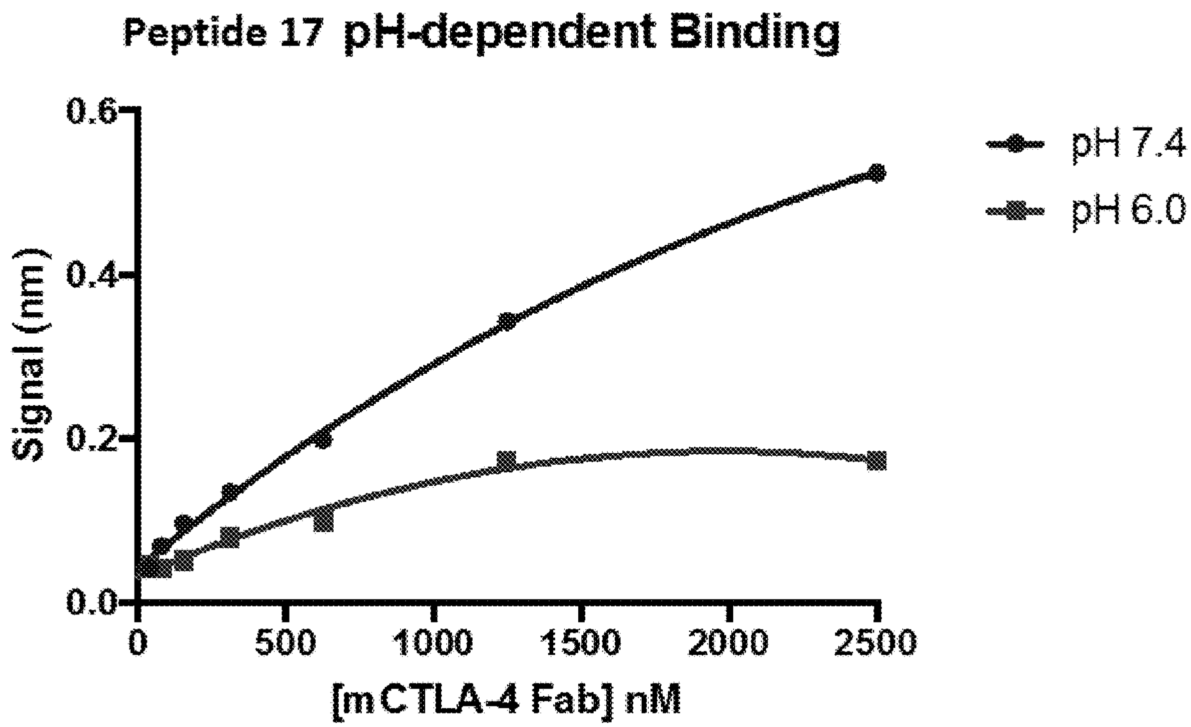
Figure 16C:
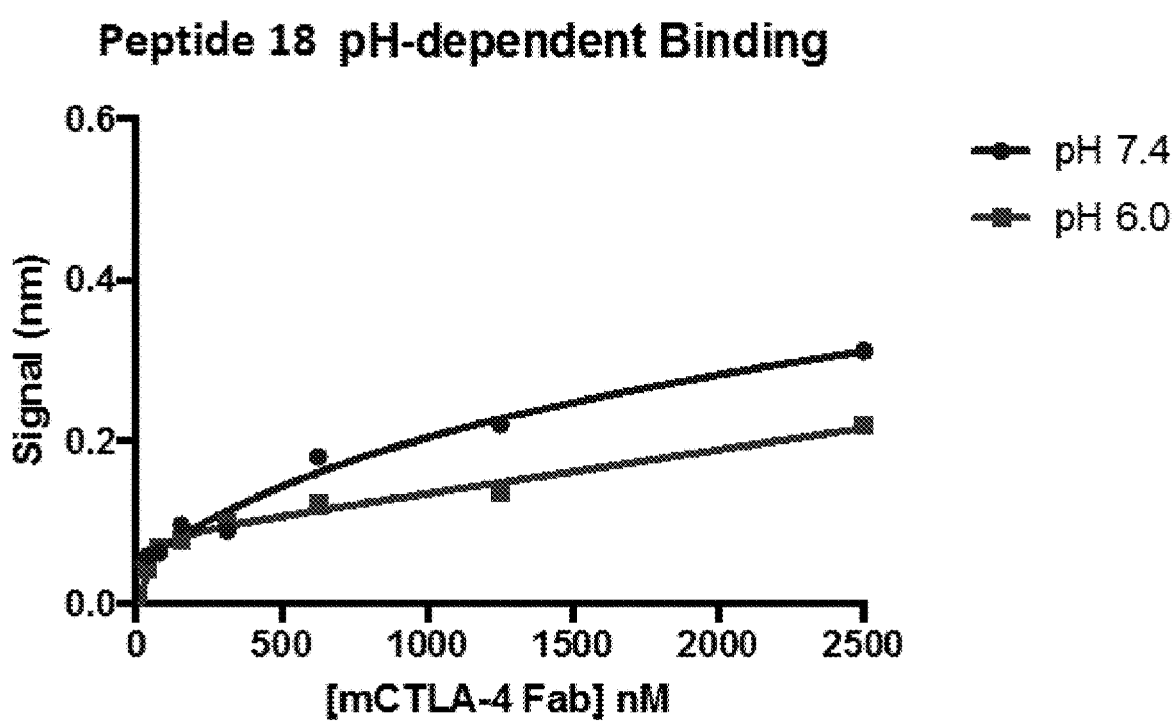
Figure 17:
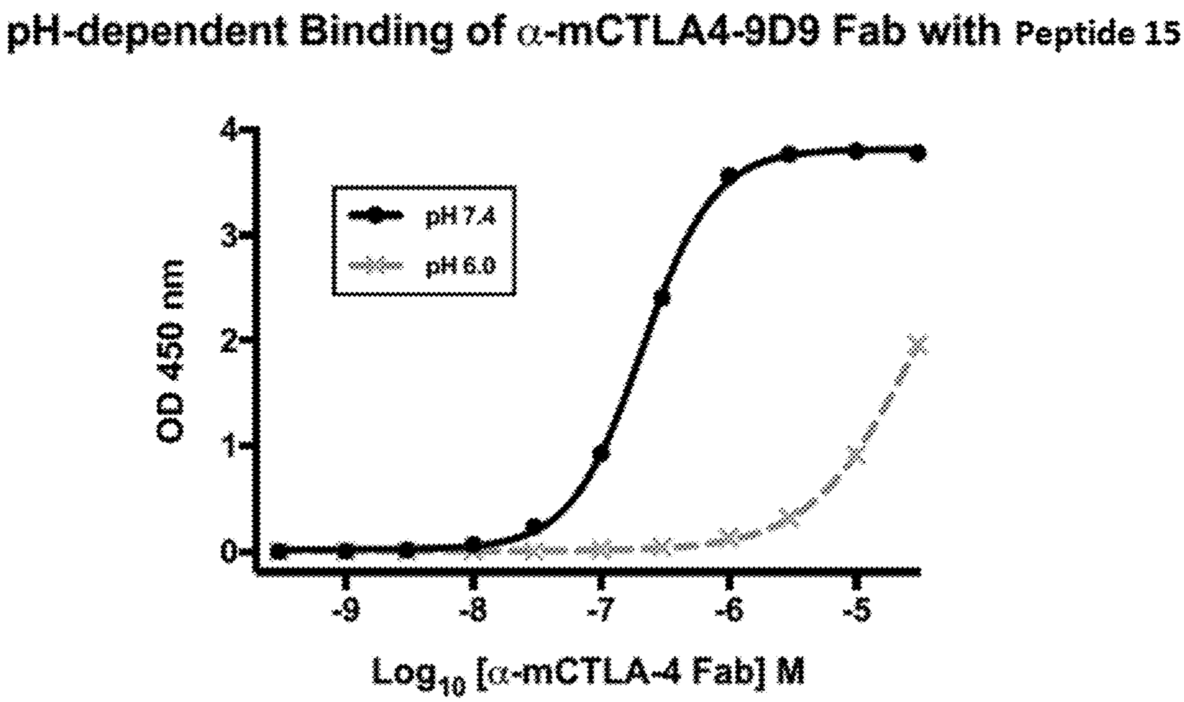
FIG. 17 illustrates pH-dependent binding of α-mCTLA-4 Fab to Peptide 15 by ELISA.
Figure 18:
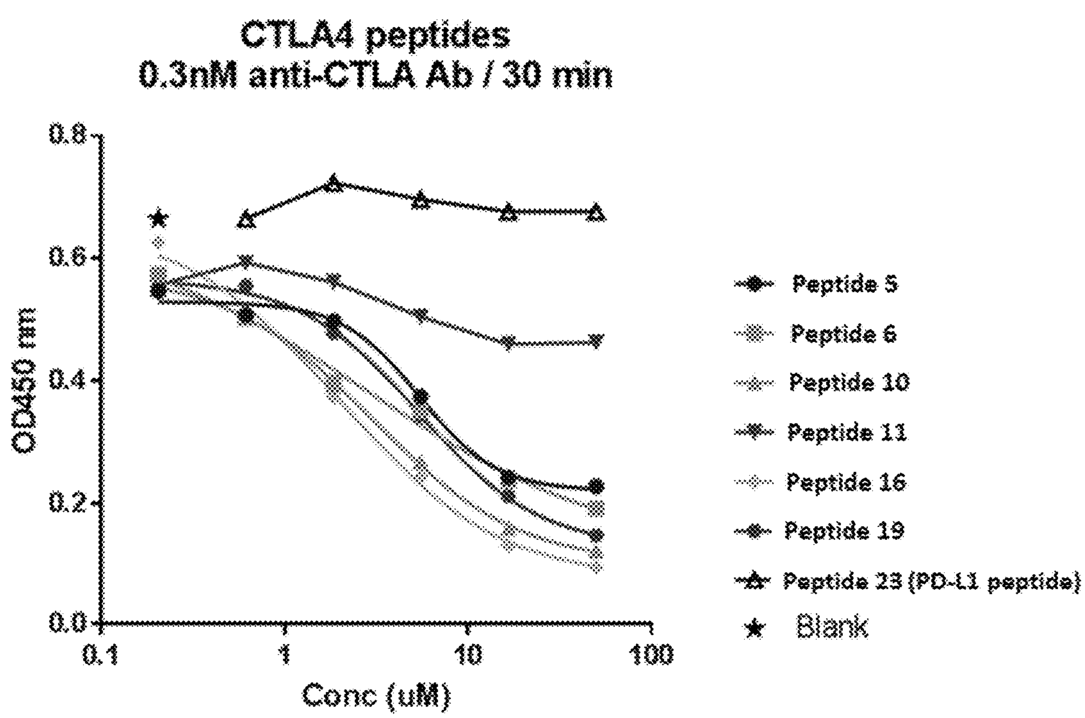
FIG. 18 illustrates CTLA4 antibody/ligand competition ELISA.
Figure 19:
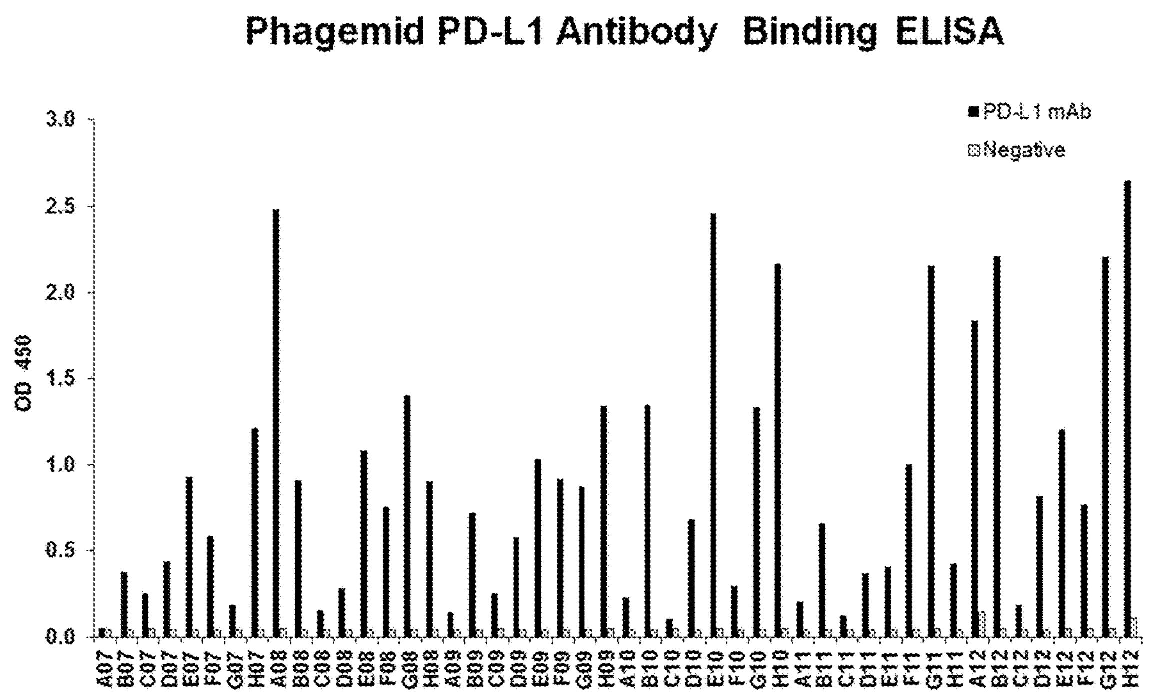
FIG. 19 illustrates a phagemid ELISA of a collection of enriched clones resulting from biopanning against PD-L1 antibody.
Figure 20:
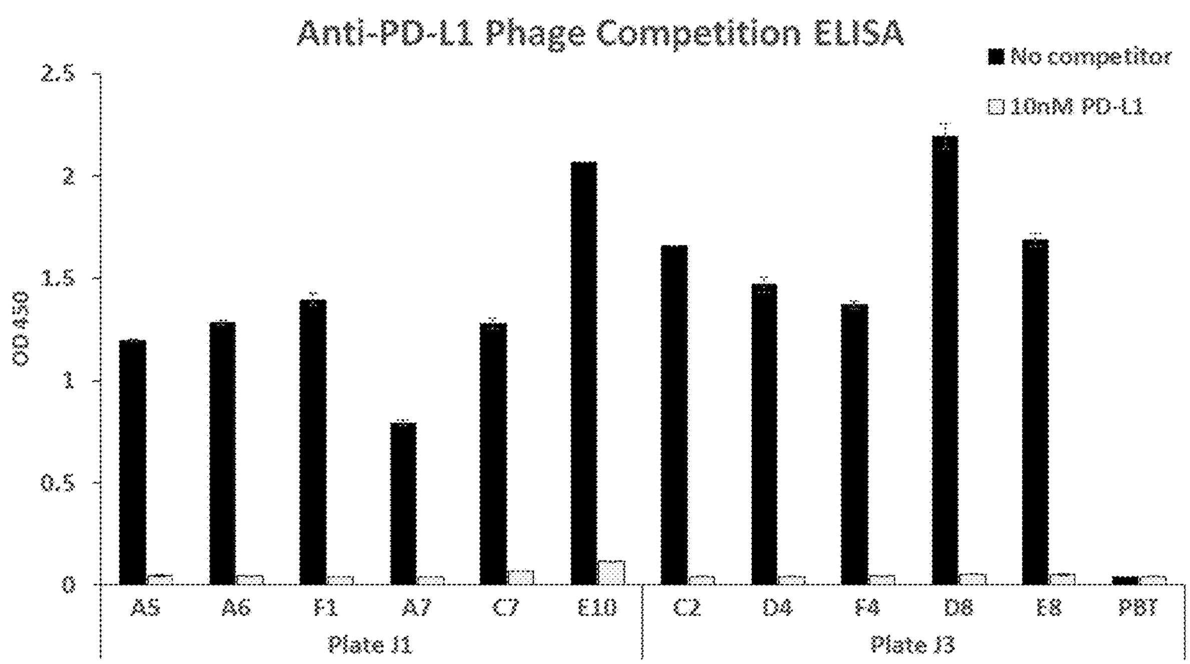
FIG. 20 illustrates anti-PD-L1 phage competition ELISA.
Figure 21:
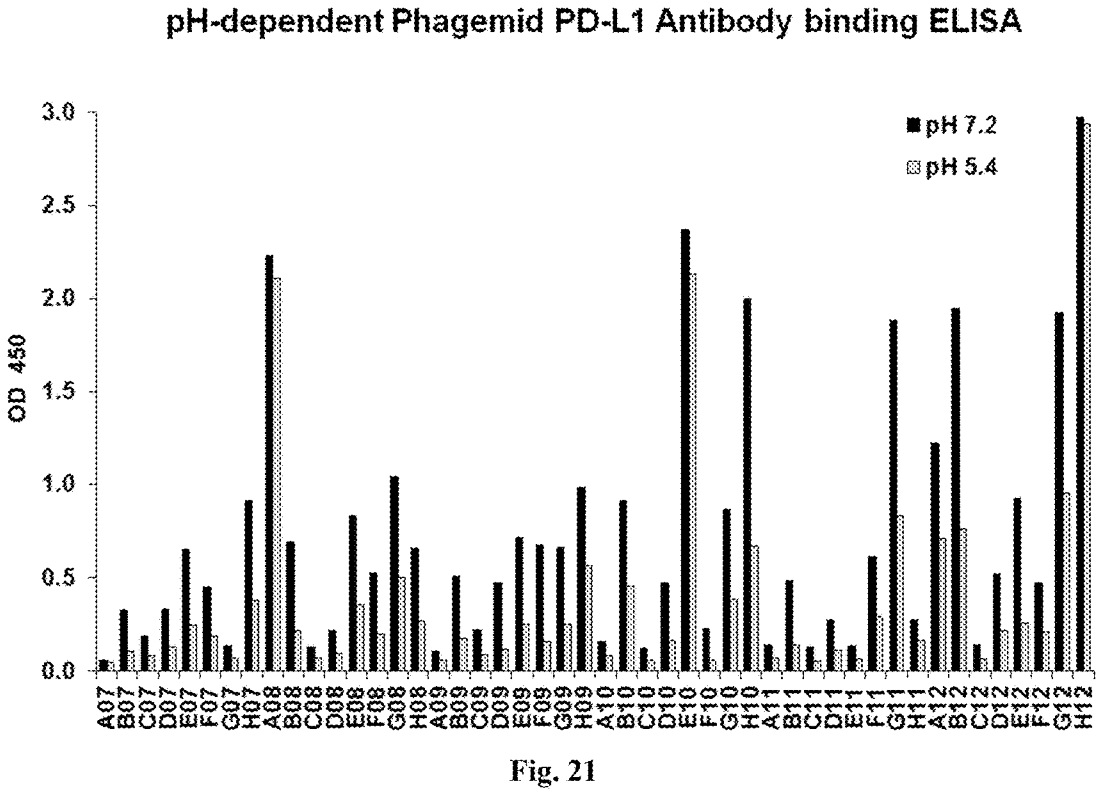
FIG. 21 illustrates pH-dependent phagemid PD-L1 antibody binding ELISA.
Figure 22:
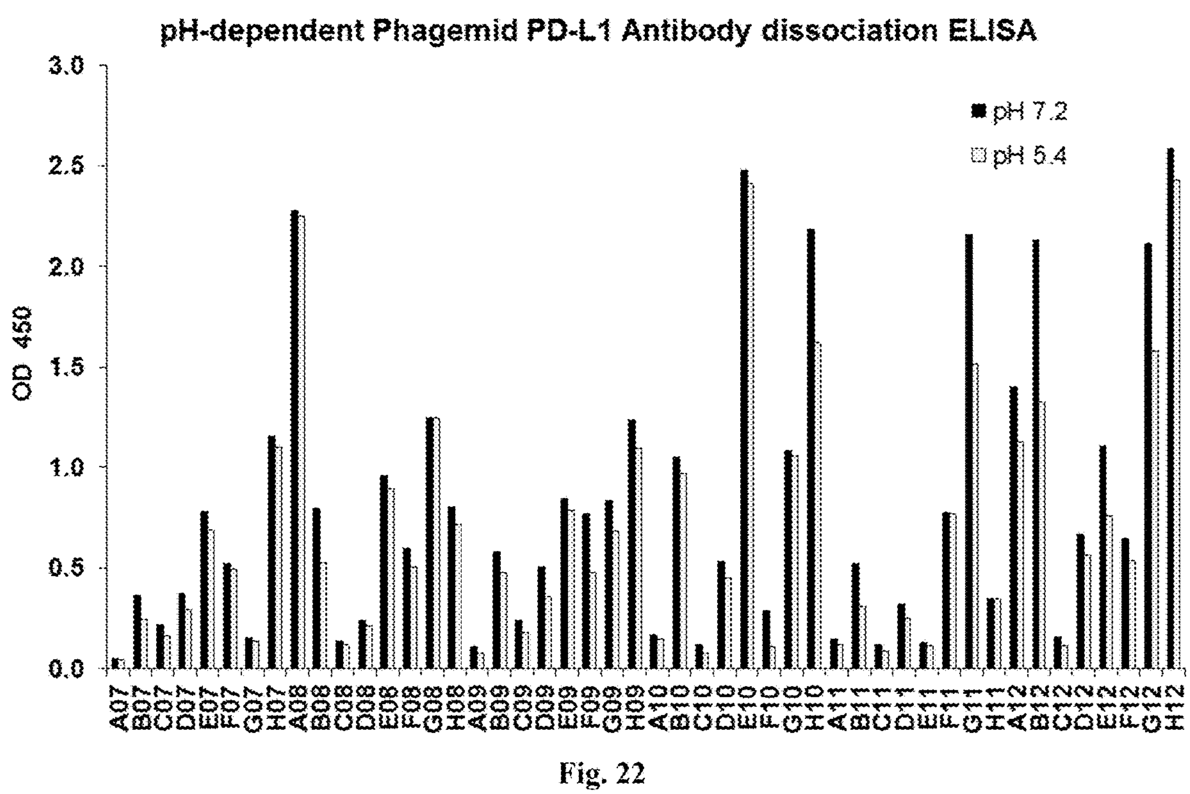
FIG. 22 illustrates pH-dependent phagemid PD-L1 antibody dissociation ELISA.
Figure 23:
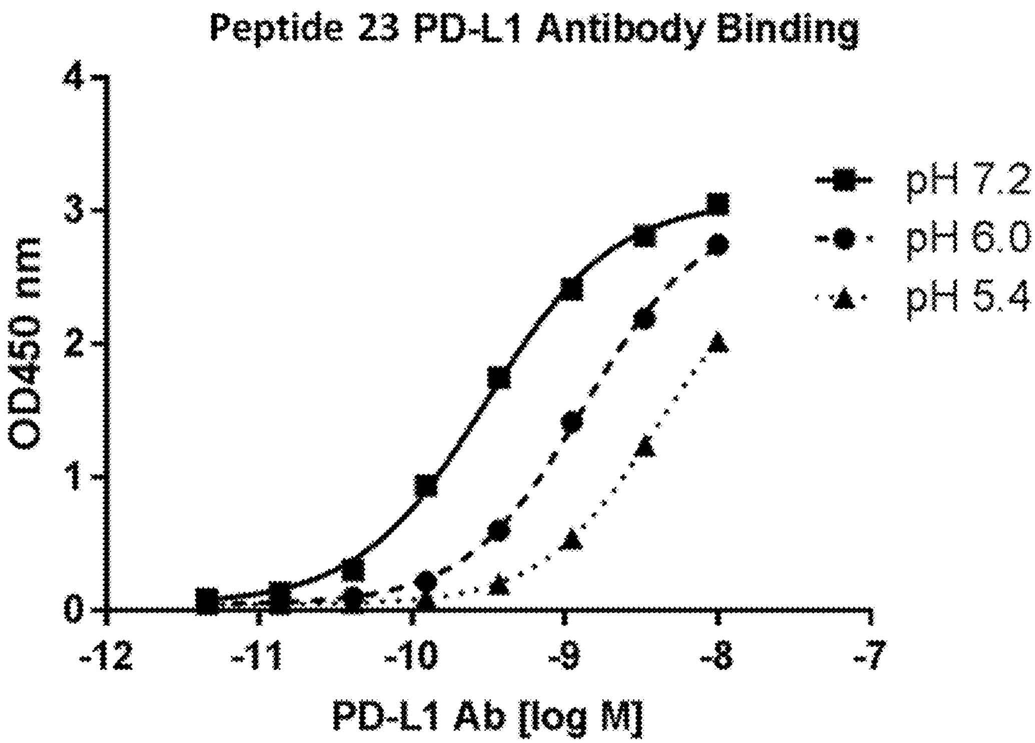
FIG. 23 illustrates Peptide 23 PD-L1 antibody binding.
Figure 24:
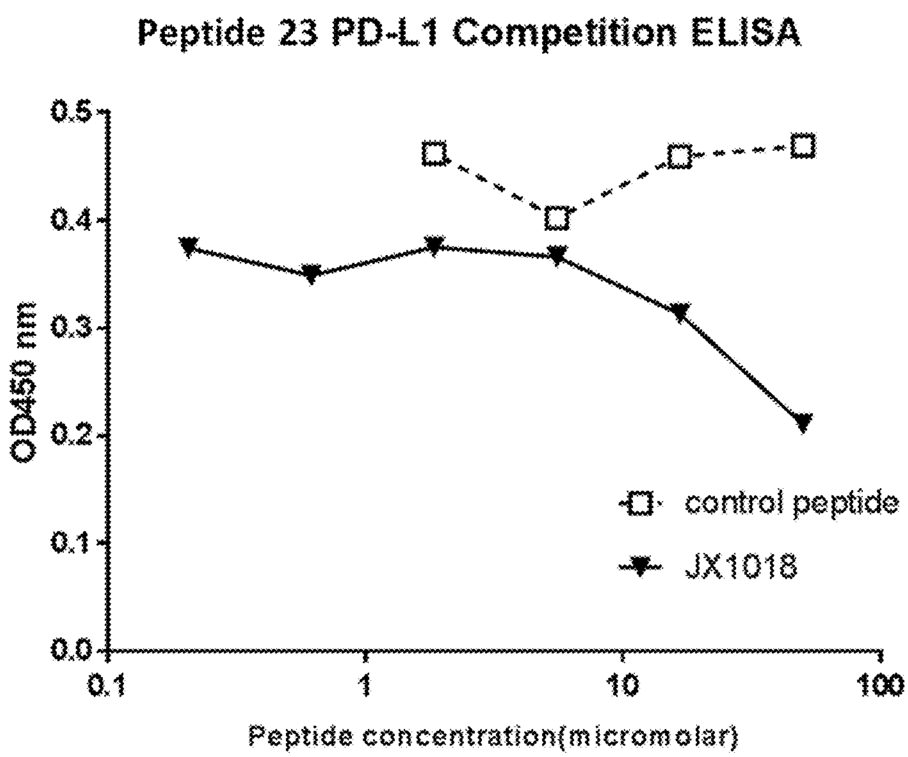
FIG. 24 illustrates Peptide 23 PD-L1 competition ELISA.
Figure 25:
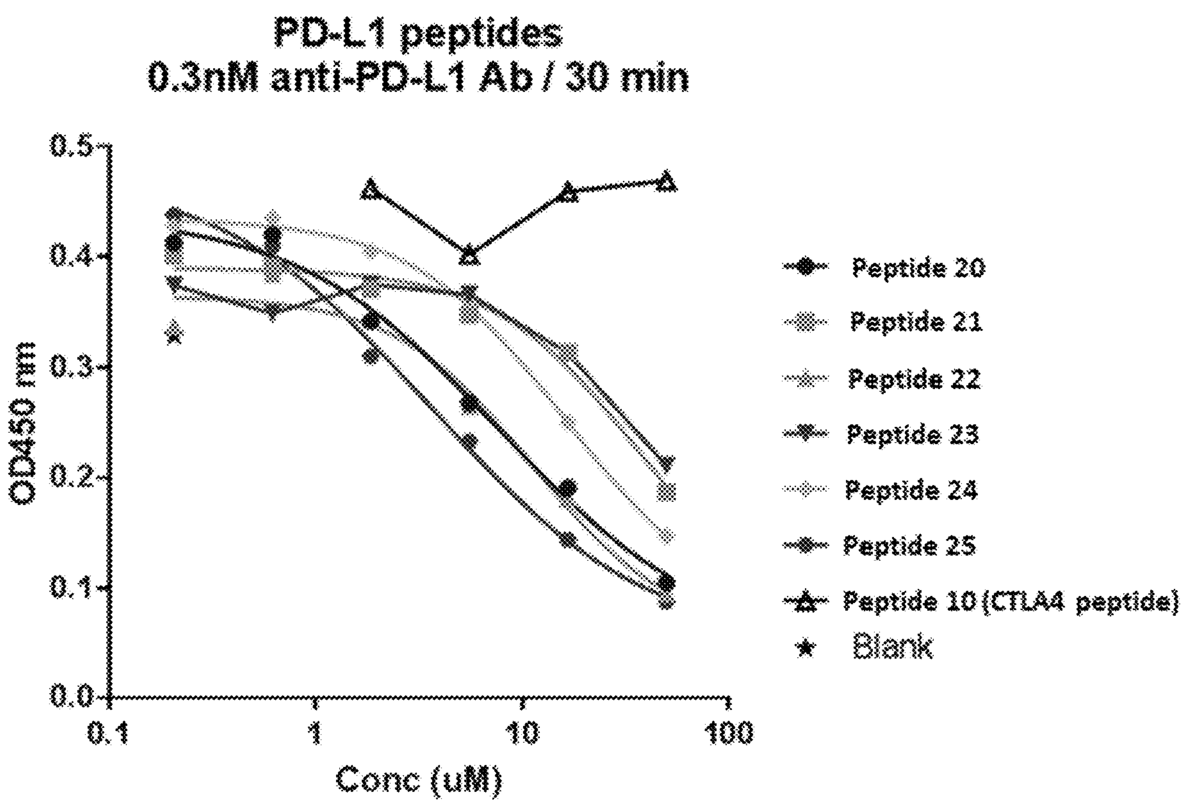
FIG. 25 illustrates PD-L1 antibody/ligand competition ELISA.

Protein-based therapies, including antibody therapies, are effective treatments for a variety of diseases. A strategy to improve toxicity and side effects of such treatments is to engineer a peptide that binds to the protein-based therapy at physiological pH, but does not bind to the protein-based therapy at acidic pH. While peptides have been shown to bind to antibodies with varying affinities, peptides which bind to antibodies in a pH dependent manner are not known. These pH-dependent peptides enable the protein-based therapy to be activated in certain acidic microenvironments while not affecting healthy tissues.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

As used herein, "physiological pH" is used to refer to the pH of a non-diseased state cellular environment. In some embodiments, physiological pH is greater than pH 6.9. In some embodiments, physiological pH is about pH 7.0 to about pH 8.0. In some embodiments, physiological pH is about 7.4.

Described herein are modified antibodies, pharmaceutical compositions thereof, as well as nucleic acids, and methods for discovering the same.

The modified antibodies described herein are connected by a linking moiety to a peptide. The peptide is designed to reduce binding of the modified antibody to its target antigen when at physiological pH. At acidic pH, for example at a tumor microenvironment, the peptide does not reduce binding of the modified antibody to its target antigen. The peptide is designed to activate the modified antibody at tumor microenvironments, thus improving the safety profile of such therapies. While antibody-based therapies have proven effective for some diseases in some cases, there is a need for increased targeting of antibodies to the disease site to reduce systemic-based toxicities.

Disclosed herein, in certain embodiments, are modified antibodies comprising a formula:

A-L-P wherein A is an antibody or antibody fragment that binds to a target antigen, P is a peptide that reduces binding of A to the target antigen at physiological pH, and that does not reduce binding of A to the target antigen at acidic pH, and L is a linking moiety that connects A to P at physiological pH and in a tumor microenvironment and L is bound to A outside an antigen binding site.

Peptide (P)

The peptide of the modified antibodies, in some embodiments, reversibly binds to A in such a way that P sterically blocks, inhibits, or reduces the binding of affinity of A for its target antigen at physiological pH. In some embodiments, P reversibly binds to A through ionic, electrostatic, hydrophobic, Pi-stacking, or H-bonding interactions, or a combination thereof. In some embodiments, P binds to the antigen binding site of A at physiological pH. In some embodiments, P binds to A at amino acid residues which are near the antigen binding site of A. In some embodiments, P binds to amino acid residues within the antigen binding site.

In some embodiments, at acidic pH, P is not reversibly bound to the antigen binding site of A. In some embodiments, at acidic pH, P is not reversibly bound to amino acid residues near the antigen binding site of A. The peptide activates the modified antibody at acidic pH by exposing the antigen binding site of A for engagement with its respective target antigen. In some cases, P has a different conformation at acidic pH, compared to the conformation of P at physiological pH. In some embodiments, at acidic pH, P does not form any interactions with A. In some embodiments, at acidic pH, P does not form any interactions with the linking moiety (L). In some embodiments, at acidic pH, P forms an interaction with L. In some embodiments, P and L reversibly bind through ionic, electrostatic, hydrophobic, Pi-stacking, or H-bonding interactions, or a combination thereof.

In some cases, P comprises a peptide sequence. In some cases, P comprises a peptide sequence disclosed in Table 1. In some cases, P comprises a peptide sequence at least 80% identical to a peptide sequence disclosed in Table 1. In some cases, P comprises a peptide sequence at least 90% identical to a peptide sequence disclosed in Table 1. In some cases, P comprises a peptide sequence at least 95% identical to a peptide sequence disclosed in Table 1. In some cases, the peptides disclosed herein are linear peptides. In some cases, the peptides disclosed herein are cyclic peptides.

TABLE 1

Peptide Sequences (P)

| Peptide ID | Sequence | SEQ ID NO |
|---|---|---|
| CTLA4 peptides | | |
| Peptide 1 | TLDDMSHVILYA | 29 |
| Peptide 2 | VISDNHQIVWDL | 30 |
| Peptide 3 | LTTQDHPLTILL | 31 |
| Peptide 4 | GGWICHWLEPQEACTY | 32 |
| Peptide 5 | GGCFEEHEQLVFQTHC | 33 |
| Peptide 6 | GGCILPGQHESQAIAC | 34 |
| Peptide 7 | GGCLSQMDFHDWLQYC | 35 |
| Peptide 8 | GGTDCYLWDYKASCHQ | 36 |
| Peptide 9 | GGKCDSLSYWQEIECS | 37 |
| Peptide 10 | GGADCLLHDWDSACQI | 38 |
| Peptide 11 | MQNVDEAPPLLL | 39 |
| Peptide 12 | TNDWQGLLLNVF | 40 |
| Peptide 13 | GGCQDSMFHHPNHC | 41 |
| Peptide 26 | GGCGMHQHPLFVDC | 42 |
| Peptide 14 | GGCSLSQHPNHSDC | 43 |
| Peptide 15 | GGPCNQVECHHQFT | 44 |
| Peptide 16 | GGCPSLHPQWIHVC | 45 |
| Peptide 17 | GGCFDSANQHPNIVIC | 46 |
| Peptide 18 | GGCHQDIEMPIYWC | 47 |
| Peptide 19 | GGCQIHDPHTWHLC | 48 |
| PD-L1 peptides | | |
| Peptide 20 | QLFYPSTYHIID | 49 |
| Peptide 27 | QVSPLYFYEELA | 50 |
| Peptide 21 | HQALLDFYGDY | 51 |
| Peptide 22 | GGMCHELFYSNLNWCQ | 52 |
| Peptide 23 | GGHCVDMVDFYQQTCQ | 53 |
| Peptide 28 | VDLLDGSLQDFY | 54 |
| Peptide 29 | GGLCSTFYEPQVDICY | 55 |
| Peptide 30 | SDFSGLLFYDYQ | 56 |
| Peptide 31 | GGCVHFFHHQRPDC | 57 |
| Peptide 24 | GGCHNKSGLFYHYC | 58 |
| Peptide 25 | GGCFYPGHHHQLLC | 59 |

In some embodiments, P comprises an amino acid sequence selected from the group consisting of Peptide 1, Peptide 2, Peptide 5, Peptide 6, Peptide 10, Peptide 13, Peptide 26, Peptide 14, Peptide 15, Peptide 20, Peptide 27, Peptide 21, Peptide 22, Peptide 23, Peptide 28, Peptide 29, Peptide 30, Peptide 31, and Peptide 24. In some embodiments, P comprises an amino acid sequence selected from the group consisting of Peptide 10, Peptide 13, Peptide 26, Peptide 14, Peptide 15, Peptide 27, Peptide 22, Peptide 23, and Peptide 31. In some embodiments, P comprises an amino acid sequence selected from the group consisting of Peptide 15 and Peptide 23. In some embodiments, P comprises an amino acid sequence of Peptide 15. In some embodiments, P comprises an amino acid sequence of Peptide 23.

In some embodiments, P is designed to incorporate amino acid residues which cause a conformational change when triggered by an environmental change. In some cases, the environmental change is the difference in pH from normal, healthy tissue to an acidic pH that is found at tumor microenvironments.

Cancer cells in a solid tumor are able to form a tumor microenvironment in their surroundings to support the growth and metastasis of the cancer cells. A tumor microenvironment is often hypoxic. As the tumor mass increases, the interior of the tumor grows farther away from existing blood supply, which leads to difficulties in fully supplying oxygen to the tumor microenvironment. As a result, the tumor cells tend to rely on energy generated from lactic acid fermentation, which does not require oxygen. As a consequence of using lactic acid fermentation is that the tumor microenvironment is acidic (approximately pH 6.0-6.9) in contrast to other parts of the body which are typically either neutral or slightly basic. For example, human blood plasma has a pH of about 7.4.

In some embodiments, P contains at least one histidine residue. In some embodiments, at physiological pH, at least one histidine residue of P forms a binding interaction with at least one amino acid residue of the antigen binding site of A. In some embodiments, at physiological pH, at least one histidine residue of P forms a binding interaction with at least one amino acid residue that is near the antigen binding site of A. In some embodiments, at acidic pH, at least one histidine residue of P forms a binding interaction with a glutamic acid or aspartic acid located on L.

In some embodiments, P contains more than one histidine residue. In some embodiments, P contains at least two histidine residues. In some embodiments, at physiological pH, at least two histidine residues of P form a binding interaction with an amino acid residue of the antigen binding site of A. In some embodiments, at physiological pH, at least two histidine residues of P form a binding interaction with an amino acid residue that is near the antigen binding site of A. In some embodiments, at physiological pH, at least two histidine residues of P form binding interactions with amino acid residues that are at or near the antigen binding site of A. In some embodiments, at acidic pH, at least two histidine residues of P form a binding interaction with a glutamic acid or aspartic acid located on L.

In some embodiments, P contains at least two charged amino acid residues. In some embodiments, P contains at least three charged amino acid residues. In some embodiments, the charged amino acid residues are selected from the group consisting of lysine, arginine, histidine, aspartate, and glutamate. In some embodiments, the charged amino acid residues are selected from the group consisting of glutamate, histidine, and aspartate. In some embodiments, P contains at least glutamate and histidine. In some embodiments, P contains histidine and aspartate. In some embodiments, P contains aspartate and glutamate. In some embodiments, P contains at least one histidine and at least two aspartate residues. In some embodiments, P contains at least two histidine and at least one glutamate residues. In some embodiments, P contains at least one histidine and at least two glutamate residues. In some embodiments, P contains at least two histidine and at least one aspartate residues.

In some embodiments, P contains at least two polar amino acid residues. In some embodiments, P contains at least three polar amino acids. In some embodiments, P contains at least four polar amino acids. In some embodiments, the polar amino acid residues are selected from the group consisting of serine, threonine, cysteine, asparagine, glutamine, and tyrosine. In some embodiments, P contains at least one glutamine. In some embodiments, P contains at least two glutamines. In some embodiments, P contains at least one glutamine and at least one serine. In some embodiments, P contains at least one glutamine and at least one cysteine. In some embodiments, P contains at least one glutamine and at least one asparagine. In some embodiments, P contains at least two glutamines and at least one threonine. In some embodiments, P contains at least two glutamines, and at least one asparagine. In some embodiments, P contains at least two glutamines, at least one asparagine, and at least one cysteine. In some embodiments, P contains at least two glutamines, at least one asparagine, at least one cysteine, and at least one threonine.

In some embodiments, P contains at least one cysteine. In some embodiments, P contains at least two cysteines. In some embodiments, P contains at least three cysteines.

In some embodiments, P contains at least one glutamine and at least one methionine. In some embodiments, P contains at least two glutamines and at least one methionine. In some embodiments, P contains at least two glutamines at least one methionine, and at least one threonine.

In some embodiments, P contains at least one charged amino acid residue and at least one polar amino acid residue. In some embodiments, P contains at least one charged amino acid residue and at least two polar amino acid residues. In some embodiments, P contains at least one charged amino acid residue and at least three polar amino acid residues. In some embodiments, P contains at least two charged amino acid residues and at least one polar amino acid residues. In some embodiments, P contains at least two charged amino acid residues and at least two polar amino acid residues. In some embodiments, P contains at least two charged amino acid residues and at least three polar amino acid residues. In some embodiments, P contains at least two charged amino acid residues and at least four polar amino acid residues. In some embodiments, P contains at least three charged amino acid residues and at least one polar amino acid residues. In some embodiments, P contains at least three charged amino acid residues and at least two polar amino acid residues. In some embodiments, P contains at least three charged amino acid residues and at least three polar amino acid residues. In some embodiments, P contains at least two histidine and at least two cysteine residues. In some embodiments, P contains at least three charged amino acid residues and at least two cysteines. In some embodiments, P contains at least one histidine, at least one serine, and at least one glutamine. In some embodiments, P contains at least one histidine, at least one asparagine, and at least one glutamine.

In some embodiments, P comprises the sequence of GGX, wherein X is cysteine, alanine, proline, methionine, histidine, or leucine. In some embodiments, P comprises the sequence GGC. In some embodiments, P comprises the sequence GGP. In some embodiments, P comprises the sequence GGA. In some embodiments, P comprises the sequence GGP. In some embodiments, P comprises the sequence GGM. In some embodiments, P comprises the sequence GGH. In some embodiments, P comprises the sequence GGL.

In some embodiments, P does not contain a tryptophan residue. In some embodiments, P does not contain an arginine residue. In some embodiments, P does not contain a lysine residue. In some embodiments, P does not contain a lysine residue or an arginine residue. In some embodiments, P does not contain a lysine residue, an arginine residue, or a tryptophan residue.

In some embodiments, P comprises at least one histidine, wherein at least one hydrogen bonding amino acid residue is within two amino acid positions to the histidine. In some embodiments, the hydrogen bonding amino acid residue is serine, threonine, tyrosine, asparagine, glutamine or a combination thereof.

In some embodiments, the hydrogen bonding amino acid residue is within one amino acid position to the histidine. In some embodiments, serine is within one amino acid position to the histidine. In some embodiments, threonine is within one amino acid position to the histidine. In some embodiments, tyrosine is within one amino acid position to the histidine. In some embodiments, asparagine is within one amino acid position to the histidine. In some embodiments, glutamine is within one amino acid position to the histidine.

In some embodiments, the hydrogen bonding amino acid residue is two amino acid positions away from the histidine. In some embodiments, serine is two amino acid positions away from the histidine. In some embodiments, threonine is two amino acid positions away from the histidine. In some embodiments, tyrosine is two amino acid positions away from the histidine. In some embodiments, asparagine is two amino acid positions away from the histidine. In some embodiments, glutamine is two amino acid positions away from the histidine.

In some embodiments, P contains at least one aromatic amino acid residue. In some embodiments, P contains at least two aromatic amino acid residues. In some embodiments, P contains phenylalanine and tyrosine. In some embodiments, the phenylalanine and the tyrosine are next to each other in the amino acid sequence of P. In some embodiments, P contains two phenylalanines. In some embodiments, the phenylalanines are next to each other in the amino acid sequence of P.

In some embodiments, P is a peptide sequence at least 5 amino acids in length. In some embodiments, P is a peptide sequence at least 6 amino acids in length. In some embodiments, P is a peptide sequence at least 10 amino acids in length. In some embodiments, P is a peptide sequence at least 20 amino acids in length. In some embodiments, P is resistant to cleavage by a protease.

In some embodiments, P is not a natural binding partner of A. In some embodiments, P does not comprise a mimotope. In some embodiments, P contains a random amino acid sequence that does not share any sequence homology to the natural binding partner of A. It is advantageous to use sequences that do not share any sequence homology to the natural binding partner of A to allow for greater flexibility in the peptide design. This allows for building a larger library of candidate peptide sequences for screening. In some instances, P is a modified binding partner for A which contains amino acid changes that at least slightly decrease affinity and/or avidity of binding to A. In some embodiments, P contains no or substantially no homology to A's natural binding partner. In some embodiments, P is no more than 5%, 10%, 15%, 20%, 25%, 30%, 35%, 40%, 45%, 50%, 55%, 60%, 65%, 70%, 75%, or 80% similar to the natural binding partner of A.

In some embodiments, P comprises a modified amino acid or non-natural amino acid, or a modified non-natural amino acid, or a combination thereof. In some embodiments, the modified amino acid or a modified non-natural amino acid comprises a post-translational modification. In some embodiments P comprises a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to P including the peptide backbone, the amino acid side chains, and the terminus.

Linkine Moiety (L)

In some embodiments, L is a peptide sequence of at least 5 amino acid residues. In some embodiments, L is a peptide sequence of no more than 50 amino acids. Regarding the amino acid composition of L, peptides are selected with properties that confer flexibility and facilitate a conformational change of P during a change in pH.

In some embodiments, L comprises a peptide sequence with at least one histidine. In some embodiments, at acidic pH L is reversibly bound to P. In some embodiments, P comprises a peptide sequence with at least one aspartic acid or glutamic acid, or a combination thereof. In some embodiments, the histidine of L forms an interaction with the aspartic acid or glutamic acid of P.

In some embodiments, L is resistant to protease cleavage. For example, glycine and serine residues generally provide protease resistance. Examples of suitable linking moieties for connecting A or C to P include, but are not limited to $(GS)_n$, wherein n is an integer from 6 to 20 (SEQ ID NO: 1); $(G_2S)_n$, wherein n is an integer from 4 to 13 (SEQ ID NO: 2); $(G_3S)_n$, wherein n is an integer from 3 to 10 (SEQ ID NO: 3); and $(G_4S)_n$, wherein n is an integer from 2 to 8 (SEQ ID NO: 4); and $(G)_n$, wherein n is an integer from 12 to 40 (SEQ ID NO: 5). Additional examples include, but are not limited to, $(GGGSGSGGGGS)_n$, wherein n is an integer from 1 to 3 (SEQ ID NO: 6), or $(GGGGGPGGGGP)_n$, wherein n is an integer from 1 to 3 (SEQ ID NO: 7).

In some embodiments, L binds to P at acidic pH, for example, at a tumor microenvironment. In some embodiments, at acidic pH, L is reversibly bound to P. In some embodiments, the interaction of L and P at acidic pH is mediated through a histidine residue on P and a glutamic acid or aspartic acid residue on L. Examples of such linking moieties include, but are not limited to, $(GGSGGD)_n$, wherein n is an integer from 2 to 6 (SEQ ID NO: 8); or $(GGSGGE)_n$, wherein n is an integer from 2 to 6 (SEQ ID NO: 9).

In some embodiments, L has a formula comprising, $(GS)_x(GGSGGD)_y(GS)_n$, wherein x is an integer from 0 to 20, y is an integer from 2 to 6, and z is an integer from 0 to 20 (SEQ ID NO: 10). In some embodiments, L has a formula comprising, $(G_2S)_x(GGSGGD)_y$ $(G_2S)_n$, wherein x is an integer from 0 to 13, y is an integer from 2 to 6, and z is an integer from 0 to 13 (SEQ ID NO: 11). In some embodiments, L has a formula comprising, $(G_3S)_x(GGSGGD)_y$ $(G_3S)_z$, wherein x is an integer from 0 to 10, y is an integer from 2 to 6, and z is an integer from 0 to 10 (SEQ ID NO: 12). In some embodiments, L has a formula comprising, $(G_4S)_x(GGSGGD)_y$ $(G_4S)_z$, wherein x is an integer from 0 to 8, y is an integer from 2 to 6, and z is an integer from 0 to 8 (SEQ ID NO: 13). In some embodiments, L has a formula comprising, $(G)_x(GGSGGD)_y$ $(G)_z$, wherein x is an integer from 0 to 40, y is an integer from 2 to 6, and z is an integer from 0 to 40 (SEQ ID NO: 14). In some embodiments, L has a formula comprising, $(GGGSGSGGGGS)_x(GGSGGD)_y$ $(GGGSGSGGGGS)_z$, wherein x is an integer from 0 to 3, y is an integer from 2 to 6, and z is an integer from 0 to 3 (SEQ ID NO: 15). In some embodiments, L has a formula comprising, $(GGGSGSGGGGP)_x(GGSGGD)_y$ $(GGGSGSGGGGP)_z$, wherein x is an integer from 0 to 3, y is an integer from 2 to 6, and z is an integer from 0 to 3 (SEQ ID NO. 16).

In some embodiments, L has a formula comprising, $(GS)_x(GGSGGE)_y(GS)_z$, wherein x is an integer from 0 to 20, y is an integer from 2 to 6, and z is an integer from 0 to 20 (SEQ ID NO: 17). In some embodiments, L has a formula comprising, $(G_2S)_x(GGSGGE)_y$ $(G_2S)_z$, wherein x is an integer from 0 to 13, y is an integer from 2 to 6, and z is an integer from 0 to 13 (SEQ ID NO: 18). In some embodiments, L has a formula comprising, $(G_3S)_x(GGSGGE)_y$ $(G_3S)_z$, wherein x is an integer from 0 to 10, y is an integer from 2 to 6, and z is an integer from 0 to 10 (SEQ ID NO: 19). In some embodiments, L has a formula comprising, $(G_4S)_x(GGSGGE)_y$ $(G_4S)_z$, wherein x is an integer from 0 to 8, y is an integer from 2 to 6, and z is an integer from 0 to 8 (SEQ ID NO: 20). In some embodiments, L has a formula comprising, $(G)_x(GGSGGE)_y(G)_z$, wherein x is an integer from 0 to 40, y is an integer from 2 to 6, and z is an integer from 0 to 40 (SEQ ID NO: 21). In some embodiments, L has a formula comprising, $(GGGSGSGGGGS)_x(GGSGGE)_y$ $(GGGSGSGGGGS)_z$, wherein x is an integer from 0 to 3, y is an integer from 2 to 6, and z is an integer from 0 to 3 (SEQ ID NO: 22). In some embodiments, L has a formula comprising, $(GGGSGSGGGGP)_x(GGSGGE)_y$ $(GGGSGSGGGGP)_z$, wherein x is an integer from 0 to 3, y is an integer from 2 to 6, and z is an integer from 0 to 3 (SEQ ID NO: 23).

Additional examples of linking moieties include, but are not limited to wherein L has a formula selected from $(GX)_n$, wherein X is serine, aspartic acid, glutamic acid, threonine, or proline and n is at least 20 (SEQ ID NO: 24); $(GGX)_n$, wherein X is serine, aspartic acid, glutamic acid, threonine, or proline and n is at least 13 (SEQ ID NO: 25); $(GGGX)_n$, wherein X is serine, aspartic acid, glutamic acid, threonine, or proline and n is at least 10 (SEQ ID NO: 26); $(GGGGX)_n$, wherein X is serine, aspartic acid, glutamic acid, threonine, or proline and n is at least 8 (SEQ ID NO: 27); $(G_zX)_n$, wherein X is serine, aspartic acid, glutamic acid, threonine, or proline and n is at least 15, and z is between 1 and 20 (SEQ ID NO: 28).

In some embodiments, L comprises a modified amino acid or non-natural amino acid, or a modified non-natural amino acid, or a combination thereof. In some embodiments, the modified amino acid or a modified non-natural amino acid comprises a post-translational modification. In some embodiments L comprises a modification including, but not limited, to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to L including the peptide backbone, or the amino acid side chains.

Antibody or Antibody Fragments (A)

In some embodiments, A is a full length antibody, a single-chain antibody, a Fab Fragment, an Fab' fragment, an (Fab')2 fragment, an Fv fragment, a divalent single chain antibody, a bispecific antibody, trispecific antibody, tetraspecific antibody, or an antibody drug conjugate.

In some embodiments A is an antagonist, agonist, conditionally active antibody, or a sweeping body.

In some embodiments, A is an antibody or antibody fragment including, but not limited to, utomilumab, urelumab, ipilimumab, tremelimumab, pembrolizumab, nivolumab, and atezolizumab. In some embodiments, A is utomilumab. In some embodiments, A is urelumab. In some embodiments, A is ipilimumab. In some embodiments, A is tremelimumab. In some embodiments, A is pembrolizumab. In some embodiments, A is nivolumab. In some embodiments, A is atezolizumab.

In some embodiments, A binds to a target antigen. In some embodiments, the target antigen includes, but is not limited to, 4-1BB, CTLA4, PD-1, and PD-L1. In some embodiments, the target antigen is 4-1BB. In some embodiments, the target antigen is CTLA4. In some embodiments, the target antigen is PD-1. In some embodiments, the target antigen is PD-L1.

In some embodiments, A contains a modification so as to increase the bioavailability, improve stability, or solubility of the modified antibody. In some embodiments, A is conjugated to polyethylene glycol, polysialic acid (PSA), HPMA copolymer, dextran, albumin, a glycosyl group or a combination thereof.

In some embodiments, A comprises a modified amino acid or non-natural amino acid, or a modified non-natural amino acid, or a combination thereof. In some embodiments, the modified amino acid or a modified non-natural amino acid comprises a post-translational modification. In some embodiments A comprises a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to A including the peptide backbone, the amino acid side chains, or the termini or terminus.

Modified Antibodies (A-L-P)

Disclosed herein, in certain embodiments, are modified antibodies comprising a formula:

A-L-P wherein A is an antibody or antibody fragment that binds to a target antigen, P is a peptide that reduces binding of A to the target antigen at physiological pH, and that does not reduce binding of A to the target antigen at acidic pH, and L is a linking moiety that connects A to P at physiological pH and in a tumor microenvironment, and L is bound to A outside an antigen binding site.

In some embodiments, A-L-P does not comprise a protease cleavage site that releases A from P in a tumor microenvironment. It is advantageous that L and P are not cleaved from the molecule so that P can bind and re-bind to A depending upon the microenvironment. For example, in a tumor microenvironment, P is not bound to A thereby exposing the antigen binding site of A to its target antigen. However, because P is not cleaved from the molecule in the tumor microenvironment, if A-L-P were to then diffuse into a non-tumor microenvironment, P can then resume binding interactions with A, thereby preventing A from interacting with its target antigen in the non-tumor microenvironment.

In some embodiments, the modified antibodies disclosed herein comprise more than one P, one for each region of the antibody that contains the antigen binding site, connected to A by L. In some instances, L for each of the Ps is the same. In some instances, L for each of the P is different. In some embodiments, the Ps for each region of the antibody that contains the antigen binding site is the same. In some embodiments, the Ps for each region of the antibody that contains the antigen binding site is different. In some embodiments, the modified antibodies disclosed herein comprise one P.

In some embodiments, P is not a natural binding partner of A. In some embodiments, P does not comprise a mimotope. In some embodiments, P contains a random amino acid sequence that does not share any sequence homology to the natural binding partner of A. It is advantageous to use sequences that do not share any sequence homology to the natural binding part of A to allow for greater flexibility in the peptide design. This allows for building a larger library of candidate peptide sequences for screening.

In some embodiments, the target antigen to which the antibody or antibody fragment (A) binds is CTLA4, peptide (P) is Peptide 15, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 10, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 13, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 26, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 14, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 1, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 2, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 5, and linking moiety (L) is GSSGGSGGSGGSGGGSGGGSGGSSGT (SEQ ID NO: 60). In some embodiments, the target antigen to which the antibody or antibody fragment (A) binds is CTLA4, peptide (P) is Peptide 6, and linking moiety (L) is GSSGGSGGSGGSGGGSGGGSGGSSGT (SEQ ID NO: 60).

In some embodiments, the antibody or antibody fragment (A) that binds to a target antigen is Atezolizumab, peptide (P) is Peptide 23, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 27, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 22, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 31, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 20, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 21, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 28, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 29, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 30, and linking moiety (L) is GSSGGSGGSGGSGGGSGGGSGGSSGT (SEQ ID NO: 60). In some embodiments, the antibody or antibody fragment (A) that binds to a target antigen is Atezolizumab, peptide (P) is Peptide 24, and linking moiety (L) is GSSGGSGGSGGSGGGSGGGSGGSSGT (SEQ ID NO: 60).

In some embodiments, the target antigen to which the antibody or antibody fragment (A) binds is PD-L1, peptide (P) is Peptide 23, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 27, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 22, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 31, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 20, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 21, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 28, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 29, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 30, and linking moiety (L) is GSSGGSGGSGGSGGGSGGGSGGSSGT (SEQ ID NO: 60). In some embodiments, the target antigen to which the antibody or antibody fragment (A) binds is PD-L1, peptide (P) is Peptide 24, and linking moiety (L) is GSSGGSGGSGGSGGGSGGGSGGSSGT (SEQ ID NO: 60).

Polynucleotides Encoding Modified Antibodies

Also provided, in some embodiments, are polynucleotide molecules encoding a modified antibody described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described antigen-binding protein. Examples of expression vectors for expression in *E. coli* are pSKK (Le Gall et al., J Immunol Methods. (2004) 285(1): 111-27) or pcDNA5 (Invitrogen) for expression in mammalian cells.

Thus, the modified antibodies as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising a modified antibody described herein, a vector comprising the polynucleotide encoding the polypeptide of the modified antibody or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the modified antibody described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the modified antibody, is attached to liposomes. In some instances, the modified antibody is conjugated to the surface of liposomes. In some instances, the modified antibody is encapsulated within the shell of a liposome. In some instances, the liposome is a cationic liposome.

The modified antibodies described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

Methods for Discovering Modified Antibodies that are Conditionally Active at Tumor Microenvironments Disclosed herein, in some embodiments, are methods for identifying peptides which reduce binding of the modified antibody to its target antigen when at physiological pH but do not affect target antigen binding at acidic pH.

In some embodiments, a modified antibody is tested for binding to a target antigen at a range of pH, from about pH 3 to about pH 12. In a further aspect, the testing step further includes testing for antigen binding within a pH range from about pH 5 to pH 10. In a further aspect, the testing step includes testing for antigen binding within a pH range from about pH 6 to pH 8. In a further aspect, the testing step further includes testing for antigen binding within a pH range from about pH 6.7 to pH 7.5.

In additional embodiments, P is identified by directed evolution techniques. In some embodiments, P is engineered to introduce one, two, or more ionizable groups which interact at protein-protein interfaces. Such ionizable groups, for example, interact with A at the antigen binding site or near the antigen binding site at physiological pH to block binding of A to its target antigen. Such ionizable groups, for example, are engineered into P using a histidine scanning library approach.

Methods for Generating Modified Antibodies

Methods for generating an antibody (or fragment thereof) for a given target are known in the art. The structure of antibodies and fragments thereof, variable regions of heavy and light chains of an antibody (VH and VL) Fv, F(ab')2, Fab fragments, single chain antibodies (scAb), single chain variable regions (scFv), complementarity determining regions (CDR), and domain antibodies (dAbs) are well understood. Methods for generating a polypeptide having a desired antigen-binding domain of a target antigen are known in the art.

Methods for modifying antibodies or antibody fragments to couple additional polypeptides are known in the art. For example, peptides and linking moieties are coupled to modify antibodies to generate the modified antibodies of the disclosure.

In some embodiments, A, L, and P are expressed in a nucleic acid construct. In some embodiments, A, L, and P are expressed in the same nucleic acid construct. In some instances, the nucleic acid constructs include, but are not limited to, constructs which are capable of expression in a prokaryotic or eukaryotic cell.

In some embodiments, P is coupled to L and A through covalent binding. For example, A and L are expressed as a single transcript, and the terminal residue of L is a cysteine. P is then coupled to L and A by a cysteine-cysteine disulfide bridge.

EXAMPLES

Example 1. Screening of Candidate Peptides

To identify peptides for conjugation to or expression with an antibody of interest, a library of candidate peptides are generated. The candidate peptides have variable amino acid sequences and variable amino acid lengths. The candidate peptides are then screened for their ability to bind to the antibody of interest at pH 7.4 and at pH 6.0. Those candidate peptides that bind to the antibody of interest at pH 6.0 are eliminated. Candidate peptides that bind to the antibody of interest at pH 7.4, but not at pH 6.0, are sequenced and motifs are analyzed.

Example 2. Screening of Modified Antibody Libraries

Libraries of candidate modified antibodies having different amino acid sequences in the peptide and linker lengths and various points of attachment to the antibody are generated.

The libraries are introduced via expression vectors resulting in display of the modified antibodies on the surface of bacterial cells. After expansion of the libraries by culture, cells displaying the modified antibodies are tested for their abilities to bind to target antigens at pH 7.4 and at pH 6.0. Cells are contacted with fluorescently labeled target antigen and the cells are sorted by FACs to isolate those cells which can bind to the fluorescently labeled target antigen at pH 6.0, but not at pH 7.4. The cells can be subjected to additional cycles by expansion by growth in culture and again by subjecting the culture to all or part of the screening steps.

Example 3. In Vitro Screening of a Modified Antibody for pH Dependent Binding Affinity for its Target Antigen An immunoabsorbent target displacement assay (TDA) is described herein for discovery and validation of a modified antibody for selective binding to its target antigen at an acidic pH. In the TDA assay, the ability of a modified antibody to bind to its target antigen is measured. The assay is conducted at pH 7.4, and then repeated at pH 6.0.

Briefly, the target antigen is adsorbed to the wells of an ELISA plate overnight at 4° C. The plate is blocked by addition of 2% non-fat dry milk in PBS, about 0.5% (v/v) Tween20 (PBST), and incubation at room temperature for about 1 hour. The plate is then washed about three times with PBST. About 50 μl of superblock is added. About 50 μl of the modified antibody is dissolved in superblock and incubated at about 37° C. for different periods of time. The plate is washed about three times with PBST. About 100 ml of anti-huIgG-HRP is added in about 2% NEM/PBST and incubated at room temperature for about 1 hour. The plate is washed about four times with PBST and about twice with PBS. The assay is developed using TMB (Thermo Scientific) as per manufacturer's instructions.

Example 4. Cytotoxicity Assay for Assessing pH Dependent Selectivity of Modified Antibodies Modified antibodies are selected which demonstrate binding to its target antigen at pH 6.0, but with minimal or no binding to its target antigen at pH 7.4 conditions. A candidate antibody, and a peptide-modified candidate antibody validated in Example 3, is tested in a cell based cytotoxicity assay.

Cell Culture: A549 (human epithelial cell line derived from a lung carcinoma tissue), or an alternative cancer cell line (DU145, LNCaP, or PC-3 cells) can be obtained from, for example, the ATCC. Human umbilical vein endothelial cells (HUVEC) can be isolated from human umbilical veins as described. (Grant et al., "Matrigel induces thymosin h 4 gene in differentiating endothelial cells", J Cell Sci 1995; 108:3685-94). HUVEC cells can be used as a positive control as a cell line that express ATP synthase on the cell surface. Cells can be cultured in DMEM (Life Technologies, Carlsbad, Calif.) with 1% penicillin streptomycin and 10% serum replacement medium 3 (Sigma, St. Louis, Mo.) to minimize the presence of plasminogen. Low-pH (6.7) medium can be prepared by reducing bicarbonate to 10 mmol/L at 5% CO2 and supplementing with 34 mmol/L NaCl to maintain osmolality or incubation of 22 mmol/L bicarbonate medium under 17% CO2 conditions. The method of lowering pH used can be varied by experimental constraints and assay.

Flow cytometry: To assure ATP synthase is functional on the cell surface of the tumor cell line, flow cytometry experiments can be performed. For example, A549 Cell lines can be cultured in varying pH medium (10, 22, and 44 mmol/L bicarbonate DMEM), under hypoxia (0.5% 02, 5% CO2, N2 balanced) versus normoxia (21% 02, 5% CO2) for 0, 12, 24, 48, and 72 hours. Live cells can be blocked, incubated with anti-β-subunit antibody, washed, blocked, incubated with a secondary goat anti-rabbit antibody-FITC (Southern Biotech, Birmingham, Ala.), and again washed, with all steps performed at 4 degrees C. Propidium iodide (BD Biosciences, San Jose, Calif.) can be included with all samples to discriminate cells with compromised membranes. The mean fluorescent intensity of FITC in 10,000 cells can be quantified by FACSCalibur flow cytometer (Becton Dickinson, Franklin Lakes, N.J.) and cells with propidium iodide uptake can be excluded to eliminate detection of mitochondrial ATP synthase on CELLQuest software (BD Biosciences).

Cell surface ATP generation assam: A549 or 1-LN cells (60,000 per well) in 96-well plates can be refreshed with medium and treated with a candidate antibody, a peptide-modified candidate antibody, anti-beta-subunit antibody, rabbit IgG raised to bovine serum albumin (Organon Teknika, West Chester, Pa.), piceatannol (a known inhibitor of ATP synthase F1 used as a positive control, Sigma), or medium alone for 30 minutes at 37 degrees C., 5% CO2. Cells can be then incubated with 0.05 mmol/L ADP for 20 seconds. Supernatants can be removed and assayed for ATP production by CellTiterGlo luminescence assay (Promega, Madison, Wis.) as described (23). Cell lysates can be similarly analyzed to confirm that intracellular pools of ATP did not vary under any conditions. Recordings can be made on the Luminoskan Ascent (Thermo Labsystems, Helsinki, Finland). Data are expressed in moles of ATP per cell based on standards determined for each independent experiment.

Cell proliferation assay: The effect of the candidate modified antibody on cancer cell lines can be assessed with a 3-(4,5-dimethylthiazol-2-yl)-5-(3-carboxymethoxyphenyl)-2-(4-sulfophenyl)-2H-tetrazolium, inner salt (MTS) proliferation assay in serum-free medium. Relative cell numbers in each well of a 96-well microplate after incubation for 20 hours, 37 degrees C., and 5% $CO_2$ in the presence or absence of the candidate antibody can be determined using the AQueous One Cell Proliferation Assay (Promega) per protocol of the manufacturer. Medium pH can be regulated at 5% $CO_2$ through bicarbonate concentration.

Assessment of cellular cytotoxicity: To quantify cell death and cell lysis, the activity of lactate dehydrogenase (LDH) released from the cytosol into supernatant can be measured with the Cytotoxicity Detection kit (Roche, Indianapolis, Ind.). Cancer cells (e.g. A549 cells)(5,000 per well) treated with a candidate antibody, a peptide-modified candidate antibody, anti-beta-subunit antibody, rabbit IgG, cariporide, and Triton X (a detergent used to permeabilize cells as a positive control) can be incubated at 37 degrees C. and 5% $CO_2$ or 17% $CO_2$ for 15 hours at neutral and low pH conditions, respectively. An index of cytotoxicity can be calculated by dividing the average absorbance from treated samples in quadruplicate by the average absorbance from untreated samples in quadruplicate corresponding to the same pH medium.

Assessment of cellular necrosis and apoptosis: To determine the mode of candidate antibody induced cell death a histone-DNA ELISA can be performed. The effects of a candidate antibody, a peptide-modified candidate antibody, anti-beta-subunit antibody, rabbit IgG, and cariporide on A549 cells (5,000 per well) can be determined using an ELISA apoptosis and necrosis assay (Roche) that is dependent on detection of extranuclear histone-DNA fragments. Apoptosis or necrosis can be determined from, respectively, the cell lysates or supernatants of quadruplicate samples after 15 hours of incubation at 37 degrees C., in the presence or absence of agents. The apoptotic or necrotic indices can be calculated by dividing the average absorbance from treated samples in quadruplicate by the average absorbance from untreated samples in quadruplicate corresponding to the same pH medium. Medium pH can be regulated by incubation at 5% CO2 or 17% $CO_2$.

Example 5. Biopanning

Biopanning with m13 phagemid p8 or p3 displayed peptide libraries was either performed with Fc immobilized anti-mouse CTLA-4 antibody (clone 9D9) on 96-well ELISA plates or with biotin-conjugated antibody immobilized on streptavidin coated paramagnetic beads. Following binding to target and washing steps, specifically bound phage were recovered by elution at pH 2.2 and in some instances recovery occurred through the use of acidic buffers of higher pH levels. Enrichment of specific binding clones was accomplished by 3-4 rounds of successive biopanning and amplification. After 3 or 4 rounds of biopanning phage pools were infected into TG1 cells and plated out on LB-ampicillin/agar plates for clonal isolation and subsequent characterization.

Example 6. Phagemid Hit Identification ELISA

For hit identification, individual colonies were grown in 96-deep well plates for 2-4 hours and infected with helper phage to produce peptide displayed phagemid following an overnight growth. The next day the deep well plates were centrifuged to separate the soluble phagemid from the *E. coli* cells. The phagemid containing supernatants were then combined with PBS-Tween 20 (0.05%)+BSA (1%) pH neutral blocking buffer and incubated in previously antibody (anti-mouse CTLA-4, clone 9D9) coated and blocked wells. After binding at 4 degrees the plates were washed and specifically bound phage were detected by anti-m13 HRP conjugated antibodies using standard TMB-based chromogenic ELISA procedures. Daughter plates or individual wells were subjected to standard DNA sequencing for peptide identification.

Example 7. Phagemid Competition ELISA Assay

Phagemid peptide clones were next tested to determine whether they bound within the antigen binding space of the antibody, by target-based competition assay. Antibody (anti-mouse CTLA-4, clone 9D9) immobilized and blocked 96-well ELISA plates similar to above were prepared. Mouse CTLA-4 was added to the well to block the antigen binding site. After a brief incubation period phagemid supernatants were added to the wells. Following an incubation at 4 degrees the plates were washed and specifically bound phage were detected by anti-m13 HRP conjugated antibodies using standard TMB-based chromogenic ELISA procedures. Phagemid clones binding within the antigenic binding pocket would be blocked and be identified by a decreased ELISA signal, compared to a well lacking previous antigen blockade.

Example 8. Phagemid pH "Binding" ELISA

To assess the pH dependent binding attributes of each of the individual clones, an ELISA similar to that described above was performed, but instead of combining the supernatants into pH neutral buffers they were combined with acidic pH buffered blocking buffer to achieve acidic pH levels such as pH 5.4 and then transferred into antibody (anti-mouse CTLA-4, clone 9D9) coated and blocked wells.

Following incubation at 4 degrees the plates were washed and then all subsequent steps buffers used were neutral pH. As before, the specifically bound phage were similarly detected by anti-m13 HRP conjugated antibodies using standard TMB-based chromogenic ELISA procedures.

Table 2 below shows the ELISA results for pH-dependent phagemid 9D9 Antibody binding.

TABLE 2 pH-dependent phagemid 9D9 Antibody binding ELISA.

| Plate | ELISA signal | | ELISA signal |
|---|---|---|---|
| wells | pH 7.2 | pH 5.4 | Ratio 5.4:7.2 |
| A07 | 2.173 | 1.546 | 0.712 |
| B07 | 0.567 | 0.177 | 0.312 |
| C07 | 1.700 | 0.799 | 0.470 |
| D07 | 1.753 | 1.136 | 0.648 |
| E07 | 0.501 | 0.219 | 0.436 |
| F07 | 0.477 | 0.054 | 0.113 |
| G07 | 0.738 | 0.062 | 0.084 |
| H07 | 1.687 | 1.096 | 0.650 |
| A08 | 1.616 | 0.215 | 0.133 |
| B08 | 0.125 | 0.045 | 0.359 |
| C08 | 1.956 | 1.222 | 0.625 |
| D08 | 1.004 | 0.278 | 0.276 |
| E08 | 1.153 | 0.119 | 0.103 |
| F08 | 2.415 | 1.651 | 0.684 |
| G08 | 2.291 | 2.037 | 0.889 |
| H08 | 1.099 | 0.539 | 0.491 |
| A09 | 0.837 | 0.329 | 0.392 |
| B09 | 2.283 | 1.836 | 0.804 |
| C09 | 1.352 | 0.220 | 0.162 |
| D09 | 1.055 | 0.260 | 0.247 |
| E09 | 0.538 | 0.059 | 0.110 |
| F09 | 0.949 | 0.264 | 0.278 |
| G09 | 1.266 | 0.516 | 0.408 |
| H09 | 0.422 | 0.066 | 0.156 |
| A10 | 1.088 | 0.304 | 0.279 |
| B10 | 1.147 | 0.495 | 0.431 |
| C10 | 1.530 | 0.234 | 0.153 |
| D10 | 1.842 | 1.105 | 0.600 |
| E10 | 0.844 | 0.276 | 0.327 |
| F10 | 2.154 | 1.645 | 0.764 |
| G10 | 1.034 | 0.375 | 0.363 |
| H10 | 0.425 | 0.174 | 0.409 |
| A11 | 0.626 | 0.217 | 0.347 |
| B11 | 0.851 | 0.306 | 0.360 |
| C11 | 0.861 | 0.181 | 0.211 |
| D11 | 1.358 | 0.570 | 0.420 |
| E11 | 0.990 | 0.430 | 0.434 |
| F11 | 1.699 | 0.958 | 0.564 |
| G11 | 0.053 | 0.049 | 0.915 |
| H11 | 2.369 | 2.110 | 0.891 |
| A12 | 0.518 | 0.257 | 0.496 |
| B12 | 0.331 | 0.148 | 0.447 |
| C12 | 0.295 | 0.049 | 0.168 |
| D12 | 1.103 | 0.208 | 0.189 |
| E12 | 1.263 | 0.246 | 0.195 |
| F12 | 0.593 | 0.283 | 0.478 |
| G12 | 1.064 | 0.432 | 0.406 |
| H12 | 3.031 | 1.749 | 0.577 |

Example 9. Phagemid "Dissociation" Assay

To determine pH dependent dissociation attributes of the individual phagemid displayed peptides, an ELISA similar to that described above was performed. Phagemid supernatants were combined with neutral pH PBS-Tween 20, BSA containing blocking buffer and then transferred into antibody (anti-mouse CTLA-4, clone 9D9) coated and blocked wells. After binding at 4 degrees the plates were washed extensively. In the next step the phage were incubated with either neutral or acidic pH buffers, such as pH 5.4 for approximately 30 minutes and then washed again at neutral pH. As described previously the specifically bound phage were similarly detected by anti-m13 HRP conjugated antibodies using standard TMB-based chromogenic ELISA procedures.

Table 3 below shows the ELISA results for pH-dependent phagemid 9D9 Antibody dissociation.

TABLE 3 pH-dependent phagemid 9D9 Antibody dissociation ELISA.

| | ELISA signal | | ELISA signal |
|---|---|---|---|
| Plate wells | pH 7.2 | pH 5.4 | Ratio 5.4:7.2 |
| A07 | 1.996 | 2.054 | 1.029 |
| B07 | 0.578 | 0.377 | 0.652 |
| C07 | 1.681 | 1.487 | 0.885 |
| D07 | 1.851 | 1.775 | 0.959 |
| E07 | 0.474 | 0.444 | 0.937 |
| F07 | 0,400 | 0.063 | 0.156 |
| G07 | 0.633 | 0.072 | 0.113 |
| H07 | 1.611 | 1.541 | 0.956 |
| A08 | 1.449 | 0.494 | 0.341 |
| B08 | 0.113 | 0.043 | 0.386 |
| C08 | 1.948 | 1.818 | 0.933 |
| D08 | 0.947 | 0.575 | 0.607 |
| E08 | 1.068 | 0.182 | 0.170 |
| F08 | 2.421 | 1.986 | 0.820 |
| G08 | 2.305 | 2.250 | 0.976 |
| H08 | 1.007 | 0.980 | 0.974 |
| A09 | 0.747 | 0.689 | 0.922 |
| B09 | 2.372 | 2.129 | 0.897 |
| C09 | 1.302 | 0.388 | 0.298 |
| D09 | 0.987 | 0.617 | 0.625 |
| E09 | 0.477 | 0.072 | 0.150 |
| F09 | 0.866 | 0.556 | 0.642 |
| G09 | 1.169 | 1.022 | 0.874 |
| H09 | 0.302 | 0.054 | 0.179 |
| A10 | 0.964 | 0.542 | 0.562 |
| B10 | 1.250 | 0.833 | 0.666 |
| C10 | 1.507 | 0.346 | 0.230 |
| D10 | 1.896 | 1.815 | 0.957 |
| E10 | 0.755 | 0.524 | 0.694 |
| F10 | 2.184 | 2.180 | 0.998 |
| G10 | 0.984 | 0.918 | 0.933 |
| H10 | 0.371 | 0.354 | 0.955 |
| A11 | 0.562 | 0.468 | 0.831 |
| B11 | 0.928 | 0.714 | 0.770 |
| C11 | 0.651 | 0.467 | 0.717 |
| D11 | 1.383 | 0.978 | 0.707 |
| E11 | 0,912 | 0.919 | 1.008 |
| F11 | 1.581 | 1.595 | 1.009 |
| G11 | 0.049 | 0.042 | 0.862 |
| H11 | 2.382 | 2.320 | 0.974 |
| A12 | 0.474 | 0.457 | 0.964 |
| B12 | 0.380 | 0.278 | 0.732 |
| C12 | 0.283 | 0.048 | 0.169 |
| D12 | 1.055 | 0.266 | 0.252 |
| E12 | 1.159 | 0.363 | 0.313 |
| F12 | 0.505 | 0.490 | 0.969 |
| G12 | 0.857 | 0.745 | 0.870 |
| H12 | 2.366 | 0.184 | 0.078 |

Example 10. Peptide Antibody Dissociation

To determine pH dependent antibody dissociation attributes of the individual peptides identified through biopanning described above, the corresponding biotinylated peptides were chemically synthesized an ELISA similar to the phagemid antibody binding example described above was performed. To begin, peptides were immobilized on neutravidin coated and blocked wells. After unbound peptides were washed away, dilution series of anti-mouse CTLA-4 antibody (clone 9D39) were added to corresponding wells of peptides. After binding at 4 degrees the plates were washed extensively as before. Next the peptides were incubated with either neutral or acidic pH buffers for approximately 30 minutes and then washed again. The specifically peptide bound antibodies were detected by either anti-mouse Fc or anti-mouse kappa chain HRP conjugated antibodies using standard TMB-based chromogenic ELISA procedures. The effects of pH upon affinity were determined by standard EC50 analysis of each of the distinct pH dilution series binding curves and comparison of their respective EC50 values.

Similar approach was taken to determine pH-dependent antibody dissociation attributes of the individual peptides to PD-L1 antibody.

TABLE 4 pH-dependent CTLA-4 antibody-peptide dissociation.

| Peptide | sequence | SEQ ID NO | EC50 [M] pH 7.2 | EC50 [M] pH 6.0 | pH 6.0: pH 7.2 EC 50 ratio |
|---|---|---|---|---|---|
| 1 | TLDDMSHVILYA | 29 | 2.9E−09 | 1.9E−08 | 6.7 |
| 2 | VISDNHQIVWDL | 30 | 1.8E−09 | 9.5E−09 | 5.2 |
| 3 | LTTQDHPLTILL | 31 | 2.2E−09 | 7.9E−09 | 3.5 |
| 4 | GGWICHWLEPQEACTY | 32 | 1.9E−09 | 4.1E−09 | 2.1 |
| 5 | GGCFEEHEQLVFQTHC | 33 | 2.5E−10 | 2.5E−09 | 9.6 |
| 6 | GGCILPGQHESQAIAC | 34 | 1.2E−10 | 1.7E−09 | 15.0 |
| 7 | GGCLSQMDFHDWLQYC | 35 | 7.8E−09 | 2.5E−08 | 3.2 |
| 8 | GGTDCYLWDYKASCHQ | 36 | 2.4E−09 | 5.3E−09 | 2.2 |
| 9 | GGKCDSLSYWQEIECS | 37 | 5.9E−09 | 1.4E−08 | 2.4 |
| 10 | GGADCLLHDWDSACQI | 38 | 5.5E−11 | 8.7E−10 | 15.8 |
| 11 | MQNVDEAPPLLL | 39 | 7.0E−09 | 1.1E−08 | 1.5 |
| 12 | TNDWQGLLLNVF | 40 | 4.0E−09 | 5.1E−09 | 1.3 |
| 13 | GGCQDSMFHHPNHC | 41 | 7.4E−09 | 3.6E−08 | 4.9 |
| 26 | GGCGMHQHPLFVDC | 42 | 1.6E−10 | 3.3E−09 | 20.9 |
| 14 | GGCSLSQHPNHSDC | 43 | 4.6E−10 | 4.1E−09 | 8.9 |
| 15 | PCNQVECHHOFT | 61 | 4.3E−10 | 5.4E−09 | 12.4 |
| 23 (Control) | GGHCVDMVDFYQQTCQ | 53 | Inactive | — | — |

TABLE 5 pH-dependent PD-L1 antibody-peptide dissociation.

| Peptide | sequence | SEQ ID NO | EC50 [M] pH 7.2 | EC50 [M] pH 6.0 | EC50 [M] pH 5.4 | pH 6.0:pH 7.2 EC 50 ratio | pH 5.4:pH 7.2 EC 50 ratio |
|---|---|---|---|---|---|---|---|
| 20 | QLFYPSTYHIID | 49 | 1.3E−10 | 2.1E−10 | 8.4E−10 | 1.7 | 6.7 |
| 27 | QVSPLYFYEELA | 50 | 4.2E−10 | 9.0E−10 | 3.3E−09 | 2.2 | 7.8 |
| 21 | HQALLDFYGDY | 51 | 7.5E−10 | 1.8E−09 | 4.8E−09 | 2.5 | 6.4 |
| 22 | GGMCHELFYSNLNWCQ | 52 | 4.5E−11 | 7.0E−11 | 3.5E−10 | 1.5 | 7.8 |
| 23 | GGHCVDMVDFYQQTCQ | 53 | 3.0E−10 | 1.3E−09 | 3.9E−09 | 4.3 | 12.9 |
| 28 | VDLLDGSLQDFY | 54 | 1.8E−09 | 4.7E−09 | 9.1E−09 | 2.6 | 5.0 |
| 29 | GGLCSTFYEPQVDICY | 55 | 2.3E−10 | 4.9E−10 | 1.5E−09 | 2.1 | 6.5 |
| 30 | SDFSGLLFYDYQ | 56 | 9.5E−10 | 2.2E−09 | 5.6E−09 | 2.3 | 5.9 |
| 31 | GGCVHFFHHQRPDC | 57 | 1.6E−10 | 3.6E−10 | 1.5E−09 | 2.3 | 9.4 |
| 24 | GGCHNKSGLFYHYC | 58 | 2.0E−10 | 5.6E−10 | 1.3E−09 | 2.8 | 6.6 |
| 10 (Control) | GGADCLLHDWDSACQI | 38 | Inactive | — | — | — | — |

Example 11. Peptide Antibody Competition

To determine whether the peptides could inhibit mouse CTLA-4 from binding the 9D9 antibody a competition binding assay was utilized. Briefly, 9D9 antibody was pre-incubated against a dilution series of peptides. Following this incubation the peptide-antibody complexes were transferred to mouse CTLA-4 coated and blocked ELISA plates and incubated further. Following a brief binding period the plates were washed and target bound antibody was detected by either anti-mouse Fc or anti-mouse kappa chain HRP conjugated antibodies using standard TMB-based chromogenic ELISA procedures. The effects of competition were determined by standard IC50 analysis.

Example 12. PH-Dependent Binding Analysis by ForteBio Octet Bio-Layer Interferometry (BLI)

To determine pH-dependent binding properties of peptides to mouse anti-CTLA-4 antibody, clone 9D9, monovalent antibody Fab fragment (mCTLA-4 Fab) was used on a ForteBio Octet Red96 System. Peptides with C-terminal biotinylation were captured on ForteBio High Precision Streptavidin (SAX) biosensors at 0.4 μg/ml in 50 mM sodium phosphate buffer, pH 7.4 with 150 mM NaCl, 0.1% BSA and 0.02% Tween-20 (pH 7.4 Assay Buffer).

For analysis of neutral pH binding, after loading, sensors were base-lined in pH 7.4 Assay Buffer followed by association with mCTLA-4 Fab (2-fold dilution series starting at 2.5 μM) in pH 7.4 Assay Buffer and dissociation in pH 7.4 Assay Buffer.

For analysis of acidic pH binding, after loading, sensors were base-lined in 50 mM sodium phosphate buffer, pH 6.0 with 150 mM NaCl, 0.1% BSA and 0.02% Tween-20 (pH 6.0 Assay Buffer) followed by association with mCTLA-4 Fab (2-fold dilution series starting at 2.5 μM) in pH 6.0 Assay Buffer and dissociation in pH 6.0 Assay Buffer.

Affinity measurements were determined by ForteBio Octet analysis software using global fitting.

Example 13. Anti-mCTLA-4 (Clone 9D9) Fab Binding to Peptide 15 by ELISA

Binding of anti-mouse CTLA-4 (clone 9D9) (Bio X Cell, Cat #BE0164) Fab fragment to Peptide 15 was determined by ELISA in 96-well plate. Briefly, 100 nM Peptide 15 with C-terminal biotin was captured on Neutravidin coated plates for 1 hour in PBS-T (50 mM phosphate buffered saline pH 7.4+0.05% Tween-20)+0.5% BSA. After washing in PBS-T, mCTLA-4 Fab diluted in either pH 7.4 Binding Buffer (50 mM sodium phosphate+150 mM NaCl+0.5% BSA+0.05% Tween-20, pH 7.4) or pH 6.0 Binding Buffer (50 mM sodium phosphate+150 mM NaCl+0.5% BSA+0.05% Tween-20, pH 6.0) was captured for 1 hour. After capture, wells were washed with either pH 7.4 Binding Buffer or pH 6.0 Binding Buffer, followed by additional 5-minute incubation with the appropriate pH Binding Buffer. Detection was performed with HRP conjugated goat anti-mouse IgG H+L (Southern Biotech.) for 1 hour at 1/2000 dilution in PBS-T+0.5% BSA followed by TMB (3-minute development) with acid stop. Absorbance at 450 nm was determined and data analysis was performed in GraphPad Prism by nonlinear regression with 4-parameter logistic curve. Data is expressed as mean±SD. All ELISA steps were performed at room temperature.

Example 14. Mammalian Expression of Reformatted Antibody Peptide Fusions

This example outlines a way to reformat peptides found above into recombinant antibody fusions. Antibodies are comprised of a full length heavy chain framework complexed with an antibody light chain. The heavy chain used is either a mouse Fc gamma 2a or mouse Fc gamma 2b isotype. The full length heavy chain and light chain sequences for 9D9 (anti-CTLA-4, clone 9D9, Curran et. al) are synthesized for expression in mammalian cells. Additional light chain constructs with 9D9 binding peptides fused by flexible linkers are similarly synthesized. The individual antibody light chain constructs are co-transfected along with the heavy chain expression vector in mammalian cells. Specifically the proteins are transiently produced in HEK293 suspension cell-based systems. The resulting proteins are harvested from the media after 5-7 days and FPLC purified to >95% purity via Protein A chromatography. Proteins are dialyzed and exchanged into pH 7.4 PBS, sterile filtered, quantitated by A280 absorbance, and stored either at 4 degrees or −80 degrees for longer term storage.

Listed below are exemplary antibody sequences comprising light chain with the peptide and heavy chain sequences.

| Antibody-peptide fusion | Isotype | Light Chain + peptide | Heavy Chain |
|---|---|---|---|
| 9D9 + peptide 10 | Mouse IgG2b | Peptide 10-9D9 light chain fusion (mouse kappa) | 9D9 heavy chain (mouse IgG2b) |
| 9D9 + peptide 13 | Mouse IgG2b | Peptide 13-9D9 light chain fusion (mouse kappa) | 9D9 heavy chain (mouse IgG2b) |
| 9D9 + peptide 14 | Mouse IgG2b | Peptide 14-9D9 light chain fusion (mouse kappa) | 9D9 heavy chain (mouse IgG2b) |
| 9D9 + peptide 15 | Mouse IgG2b | Peptide 15-9D9 light chain fusion (mouse kappa) | 9D9 heavy chain (mouse IgG2b) |
| 9D9 + peptide 10 | Mouse IgG2a | Peptide 10-9D9 light chain fusion (mouse kappa) | 9D9 heavy chain (mouse IgG2a) |
| 9D9 + peptide 13 | Mouse IgG2a | Peptide 13-9D9 light chain fusion (mouse kappa) | 9D9 heavy chain (mouse IgG2a) |
| 9D9 + peptide 14 | Mouse IgG2a | Peptide 14-9D9 light chain fusion (mouse kappa) | 9D9 heavy chain (mouse IgG2a) |
| 9D9 + peptide 15 | Mouse IgG2a | Peptide 15-9D9 light chain fusion (mouse kappa) | 9D9 heavy chain (mouse IgG2a) |
| Atezolizumab + peptide 23 | Human IgG1 | Peptide 23-Atezolizumab light chain fusion (human kappa) | Atezolizumab heavy chain (human IgG1) |

9D9 light chain (mouse kappa)

(SEQ ID NO: 62)

DIVMTQTTLSLPVSLGDQASISCRSSQSIVHSNGNTYLEWYLQKPGQSPKLLIYKVSNRFSGV

PDRFSGSGSGTDFTLKISRVEAEDLGVYYCFQGSHVPYTFGGGTKLEIKRADAAPTVSIFPPS

SEQLTSGGASVVCFLNNFYPKDINVKWKIDGSERQNGVLNSWTDQDSKDSTYSMSSTLTLT

KDEYERHNSYTCEATHKTSTSPIVKSFNRNEC

Peptide 10-9D9 light chain fusion (mouse kappa)

(SEQ ID NO: 63)

GGADCLLHDWDSACQIGSSGGSGGSGGSGGGSGGGSGGSSGTDIVMTQTTLSLPVSLGDQ

ASISCRSSQSIVHSNGNTYLEWYLQKPGQSPKLLIYKVSNRFSGVPDRFSGSGSGTDFTL-KISR

VEAEDLGVYYCFQGSHVPYTEGGGTKLEIKRADAAPTVSIFPPSSEQLTSGGASVVCFLNNE

YPKDINVKWKIDGSERQNGVLNSWTDQDSKDSTYSMSSTLTLTKDEYERHNSYTCEATHK

TSTSPIVKSFNRNEC

Peptide 13-9D9 light chain fusion (mouse kappa)

(SEQ ID NO: 64)

GGCQDSMFHHPNHCGSSGGSGGSGGSGGGSGGGSGGSSGTDIVMTQTTLSLPVSLGDQAS

ISCRSSQSIVHSNGNTYLEWYLQKPGQSPKLLIYKVSNRFSGVPDRFSGSGSGTDFTLKISRV

EAEDLGVYYCFQGSHVPYTEGGGTKLEIKRADAAPTVSIFPPSSEQLTSGGASVVCFLNNEY

PKDINVKWKIDGSERQNGVLNSWTDQDSKDSTYSMSSTLTLTKDEYERHNSYTCEATHKTS

TSPIVKSFNRNEC

-continued

Peptide 14-9D9 light chain fusion (mouse kappa)

(SEQ ID NO: 65)

GGCSLSQHPNHSDCGSSGGSGGSGGSGGGSGGGSGGSSGTDIVMTQTTLSLPVSLGDQASI

SCRSSQSIVHSNGNTYLEWYLQKPGQSPKLLIYKVSNRFSGVPDRFSGSGSGTDFTLKISRVE

AEDLGVYYCFQGSHVPYTEGGGTKLEIKRADAAPTVSIFPPSSEQLTSGGASVVCFLNNEYP

KDINVKWKIDGSERQNGVLNSWTDQDSKDSTYSMSSTLTLTKDEYERHNSYTCEATHKTST

SPIVKSFNRNEC

Peptide 15-9D9 light chain fusion (mouse kappa)

(SEQ ID NO: 66)

GGPCNQVECHHQFTGSSGGSGGSGGSGGGSGGGSGGSSGTDIVMTQTTLSLPVSLGDQAS

ISCRSSQSIVHSNGNTYLEWYLQKPGQSPKLLIYKVSNRFSGVPDRFSGSGSGTDFTLKISRV

EAEDLGVYYCFQGSHVPYTEGGGTKLEIKRADAAPTVSIFPPSSEQLTSGGASVVCFLNNEY

PKDINVKWKIDGSERQNGVLNSWTDQDSKDSTYSMSSTLTLTKDEYERHNSYTCEATHKTS

TSPIVKSFNRNEC

9D9 heavy chain (mouse IgG2b)

(SEQ ID NO: 67)

EAKLQESGPVLVKPGASVKMSCKASGYTFTDYYMNWVKQSHGKSLEWIGVINPYNGDTSY

NQKFKGKATLTVDKSSSTAYMELNSLTSEDSAVYYCARYYGSWFAYWGQGTLITVSTAKT

TPPSVYPLAPGCGDTTGSSVTLGCLVKGYFPESVTVTWNSGSLSSSVHTFPALLQSGLY

TMSSSVTVPSSTWPSQTVTCSVAHPASSTTVDKKLEPSGPISTINPCPPCKECHKCPAPN

LEGGPSVFIFPPNIKDVLMISLTPKVTCVVVDVSEDDPDVRISWFVNNVEVHTAQTQTH

REDYNSTIRVVSALPIQHQDWMSGKEFKCKVNNKDLPSPIERTISKIKGLVRAPQVYIL

PPPAEQLSRKDVSLTCLVVGFNPGDISVEWTSNGHTEENYKDTAPVLDSDGSYFIYSKL

DIKTSKWEKTDSFSCNVRHEGLKNYYLKKTISRSPGK

Atezolizumab light chain (human kappa)

(SEQ ID NO: 68)

DIQMTQSPSSLSASVGDRVTITCRASQDVSTAVAWYQQKPGKAPKWYSASFLYSGVPSRF

SGSGSGTDFTLTISSLQPEDFATYYCQQYLYHPATEGQGTKVEIKRTVAAPSVFIFPPSDEQL

KSGTASVVCLLNNFYPREAKVQWKVDNALQSGNSQESVTEQDSKDSTYSLSSTLTLSKADY

EKHKVYACEVTHQGLSSPVTKSFNRGEC

Peptide 23-Atezolizumab light chain fusion (human kappa)

(SEQ ID NO: 69)

GGHCVDMVDFYQQTCQGSSGGSGGSGGSGGGSGGGSGGSSGTDIQMTQSPSSLSASVGD

RVTITCRASQDVSTAVAWYQQKPGKAPKLLIYSASFLYSGVPSRFSGSGSGTDFTLTISSLQP

EDFATYYCQQYLYHPATFGQGTKVEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLS

SPVTKSFNRGEC

Atezolizumab heavy chain (human IgG1)

(SEQ ID NO: 70)

EVQLVESGGGLVQPGGSLRLSCAASGFTFSDSWIHWVRQAPGKGLEWVAWISPYGGSTYY

ADSVKGRFTISADTSKNTAYLQMNSLRAEDTAVYYCARRHWPGGFDYWGQGTLVTVSSA

STKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREE

QYASTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

Example 15. In Vitro Cell Based pH Dependent Binding of Masked 9D9 Antibodies

Masked 9D9 antibody binding is evaluated in isogenic 293 cells that stably express mouse CTLA-4 (mCTLA-4). Briefly, parent Flp-In 293 cells that harbor a single FRT recombination site are expanded in complete culture medium (DMEM GlutaMax 10% FBS) prior to transfection. Once sufficient parent cells are grown, cells are transfected with two vectors, one encoded the Flp recombinase and the other encoded mCTLA-4 plus a hygromycin B resistance gene. Cells successfully transfected are selected using hygromycin B. After several days of growth in the presence of hygromycin B, cellular foci are picked and expanded. Expanded foci are tested for mCTLA-4 expression via flow cytometry using the unmasked 9D9 antibody. Cells that express mCTLA-4 (mCTLA-4_293) are expanded further and cryopreserved.

mCTLA-4_293 cells are then used to evaluate pH dependent binding of masked 9D9 antibodies. mCTLA-4_293 cells are grown to 50%4-75% confluence, washed, incubated in buffered EDTA, and gently scraped from the culture dish surface. Parent 293 cells are expanded in parallel and used as controls. Cells are transferred to a 15 mL falcon tube, spun down, and washed 3 times. Cells are washed with complete culture medium in the absence of bicarb, supplemented with MES and adjusted to pH 6.0, or supplemented with HEPES and adjusted to pH 7.4. Cell are concentrated then incubated with unmasked or masked 9D9 antibodies for 1 h at RT in complete culture medium plus MES pH 6.0 or HEPES pH 7.4. Cells are washed 3 times in complete culture medium plus MES pH 6.0 or HEPES pH 7.4. Cells are then fixed in buffered formalin for 15 min RT and washed 3 times in PBS pH 7.4. Cells are concentrated then incubated with secondary AlexaFluor 555 anti-mouse antibody for 1 hr at RT in PBS 5% BSA 0.1% tween. Cells are washed 3 times with PBS 0.1% tween and analyzed by flow cytometry.

Example 16. In Vivo Efficacy Evaluation of Masked 9D9 Antibodies

Efficacy of masked 9D9 antibodies is evaluated relative to parent 9D9 in C57BL/6 or BALB/c mice bearing syngeneic MC38 tumor xenografts. Briefly, mice are subcutaneously injected with 2 million MC38 tumor cells, respectively. Tumor volumes are recorded 3 times weekly. Mice bearing palpable tumors (50-75 $mm^3$) are randomized into treatment groups with comparable mean tumor volumes. Antibodies formulated in PBS pH 7.4 are administered twice weekly intraperitoneally (IP) 200 μg per dose in a volume of 200 μL (10 mg/kg IP b.i.w). Matched isotype antibodies are used as negative controls. Percent tumor growth inhibition (TGI %) is determined after two weeks of dosing for antibody treatment groups relative to isotype controls.

Example 17. Tumor Actuated Binding of Masked 9D9 Antibodies Using In Vivo Near Infrared Imaging Selective tumor binding of masked near infrared (NIR) labeled 9D9 antibodies is evaluated relative to parent NIR 9D9 in mice bearing MC38 or CT26 tumor xenografts. Antibodies are labeled with the NIR imaging probe, IRDye-800CW-NHS (IRDye 800CW-N-hydroxysuccinimide ester) according to manufacturer's instructions. Briefly, they are incubated in the dark at room temperature with IRDye800CW in 1.0 M potassium phosphate buffer (pH 9.0) for 2 hours. The unconjugated dye is removed by desalting spin columns and purified according to manufacturer's instructions. NIR masked 9D9, NIR 9D9, or NIR labeled isotype control are administered intravenously to MC38 bearing C57Bl/6 mice via the tail vein. Forty-eight hours after administration of the NIR labeled antibodies, probe uptake and tissue distribution in the tumor bearing mice is measured using a small-animal NIR scanner (IVIS Spectrum In Vivo Imaging System). During imaging, the mice are anesthetized with isoflurane gas and placed in the prone position.

Example 18. In Vivo Efficacy Evaluation of Masked Anti-CTLA-4 Antibodies

Efficacy of masked anti-CTLA-4 antibodies is evaluated relative to parent anti-CTLA-4 antibody in C57BL/6 or BALB/c mice bearing syngeneic MC38 or CT26 tumor xenografts, respectively. Mice are subcutaneously injected with 1 million CT26 or 2 million MC38 tumor cells. Tumor volumes are recorded 3 times weekly for four weeks. Mice bearing palpable tumors (50-100 $mm^3$) are randomized into treatment groups with comparable mean tumor volumes. Antibodies formulated in PBS pH 7.4 are administered twice weekly intraperitoneally (IP) 200 μg per dose in a volume of 200 μL (10 mg/kg IP b.i.w). Matched isotype antibodies are used as negative controls. Percent tumor growth inhibition (TGI %) is determined after three weeks from first dose for antibody treatment groups relative to isotype controls.

Example 19. In Vivo Safety Evaluation of Masked Anti-CTLA-4 Antibodies in Combination with Anti-PD-1 Antibodies Five-week old female NOD mice are administered masked anti-CTLA-4 antibodies, parent anti-CTLA-4 antibody, anti-PD-1 antibody, and/or isotype controls in combination at 10 mg/kg intraperitoneally each article on days 0, 4 and 7. The following six combinations are used: 1) isotype controls, 2) parent anti-CTLA-4 antibody plus isotype control, 3) masked anti-CTLA-4 antibody plus isotype control, 4) anti-PD-1 antibody plus isotype control, 5) anti-PD-1 antibody plus parent anti-CTLA-4, or 6) anti-PD-1 antibody plus masked anti-CTLA-4 antibody. Mice are monitored daily for the induction of diabetes by glucosuria plus confirmation of two consecutive blood glucose levels ≥250 mg/dL. Monitoring is continued for a minimum of 7 days until 48 hours have passed with no new incidents of glucosuria.

Example 20. In Vivo Peripheral T-Cell Activation Using Masked Anti-CTLA-4 Antibodies Alone or in Combination with Anti-PD-1 Antibody Four to six week old C57Bl/6 mice are administered masked anti-CTLA-4 antibody, parent anti-CTLA-4 antibody, isotype control, anti-PD-1 antibody plus isotype control, anti-PD-1 antibody plus parent anti-CTLA-4 antibody, or anti-PD-1 antibody plus masked anti-CTLA-4 antibody at 10 mg/kg intraperitoneally each article on days 0, 4 and 7. On day 14 animals are euthanized. Blood and spleen are harvested from animals. Blood is stored in EDTA blood collection tubes. Spleens are digested using the mouse spleen dissociation kit from Miltenyi Biotec. Lymphocytes from blood and spleen derived cells are enriched using a Ficoll gradient. Enriched lymphocytes are stained for FoxP3 followed by either Ki67 or ICOS and measured via flow cytometry. Percent Ki67 or ICOS positive cells are calculated from total number of FoxP3 positive cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for preparing a modified antibody that has reduced binding affinity for a target antigen at physiological pH relative to its binding affinity for the target antigen at acidic pH, the method comprising: 1) screening a library of peptide sequences to identify a peptide sequence that has higher binding affinity for an antibody in an unmodified form at physiological pH relative to its binding affinity for the antibody in unmodified form at acidic pH; wherein the library of peptide sequences comprises one or more peptide sequences with at least one cysteine residue, followed by 2) linking the identified peptide sequence to the antibody with a linking moiety to provide the modified antibody, wherein the modified antibody comprises the formula A-L-P, wherein A is the antibody, L is the linking moiety and P is the identified peptide sequence.

2. The method of claim 1, wherein the library of peptide sequences comprises one or more peptide sequences having an ionizable group, and wherein the ionizable group changes a charge state between the physiological pH and the acidic pH.

3. The method of claim 2, wherein the ionizable group is histidine.

4. The method of claim 1, wherein the library of peptide sequences comprises one or more peptide sequences with at least one histidine.

5. The method of claim 1, wherein the library of peptide sequences comprises one or more peptide sequences with at least one aspartate.

6. The method of claim 1, wherein the library of peptide sequences comprises one or more peptide sequences with at least one glutamate.

7. The method of claim 1, wherein the library of peptide sequences comprises one or more peptide sequences with at least two charged amino acid residues, and wherein the at least two charged amino acid residues are selected from the group consisting of aspartate, glutamate, and histidine.

8. The method of claim 1, wherein the library of peptide sequences comprises one or more peptide sequences with at least three charged amino acid residues, and wherein the at least three charged amino acid residues are selected from the group consisting of aspartate, glutamate, and histidine.

9. The method of claim 1, wherein the library of peptide sequences comprises one or more peptide sequences with at least one histidine and at least one aspartate.

10. The method of claim 1, wherein the library of peptide sequences comprises one or more peptide sequences with at least one histidine and at least one glutamate.

11. The method of claim 1, wherein the library of peptide sequences comprises one or more peptide sequences with at least one histidine, at least one aspartate, and at least one glutamate.

12. The method of claim 1, wherein the library of peptide sequences comprises one or more peptide sequences with at least two histidines, at least one aspartate, and at least one glutamate.

13. The method of claim 1, wherein the library of peptide sequences comprises one or more peptide sequences with at least two cysteines.

14. The method of claim 1, wherein the library of peptide sequences comprises one or more peptide sequences with at least one histidine and at least one cysteine.

15. The method of claim 1, wherein the library of peptide sequences comprises one or more peptide sequences with at least two histidines and at least two cysteines.

16. The method of claim 1, wherein the modified antibody has an increased binding affinity for the target antigen in a tumor microenvironment compared to the binding affinity of the modified antibody for the target antigen in a non-tumor microenvironment.

17. The method of claim 1, wherein P inhibits the binding of A to the target antigen at physiological pH and P does not inhibit the binding of A to the target antigen at acidic pH.

18. The method of claim 1, wherein the physiological pH is about pH 7.0 to about pH 8.0, and wherein the acidic pH is about pH 6.0 to about 6.9.

19. The method of claim 1, wherein the physiological pH is about pH 7.4 and the acidic pH is about pH 6.0.

* * * * *

SEQUENCE LISTING

```
Sequence total quantity: 70
SEQ ID NO: 1            moltype = AA  length = 40
FEATURE                 Location/Qualifiers
REGION                  1..40
                        note = Description of Artificial Sequence: Synthetic
                         polypeptide
VARIANT                 1..40
                        note = This sequence may encompass 6-20 'GS' repeating
                         units wherein some positions may be absent
source                  1..40
                        mol_type = protein
                        organism = synthetic construct
SEQUENCE: 1
GSGSGSGSGS GSGSGSGSGS GSGSGSGSGS GSGSGSGSGS                        40

SEQ ID NO: 2            moltype = AA  length = 39
FEATURE                 Location/Qualifiers
REGION                  1..39
                        note = Description of Artificial Sequence: Synthetic
                         polypeptide
VARIANT                 1..39
                        note = This sequence may encompass 4-13 'GGS' repeating
                         units wherein some positions may be absent
source                  1..39
                        mol_type = protein
                        organism = synthetic construct
SEQUENCE: 2
GGSGGSGGSG GSGGSGGSGG SGGSGGSGGS GGSGGSGGS                         39

SEQ ID NO: 3            moltype = AA  length = 40
FEATURE                 Location/Qualifiers
REGION                  1..40
                        note = Description of Artificial Sequence: Synthetic
                         polypeptide
VARIANT                 1..40
                        note = This sequence may encompass 3-10 'GGGS' repeating
                         units wherein some positions may be absent
source                  1..40
                        mol_type = protein
                        organism = synthetic construct
SEQUENCE: 3
GGGSGGGSGG GSGGGSGGGS GGGSGGGSGG GSGGGSGGGS                        40

SEQ ID NO: 4            moltype = AA  length = 40
FEATURE                 Location/Qualifiers
REGION                  1..40
                        note = Description of Artificial Sequence: Synthetic
                         polypeptide
VARIANT                 1..40
                        note = This sequence may encompass 2-8 'GGGGS' repeating
                         units wherein some positions may be absent
source                  1..40
                        mol_type = protein
                        organism = synthetic construct
SEQUENCE: 4
GGGGSGGGGS GGGGSGGGGS GGGGSGGGGS GGGGSGGGGS                        40

SEQ ID NO: 5            moltype = AA  length = 40
FEATURE                 Location/Qualifiers
REGION                  1..40
                        note = Description of Artificial Sequence: Synthetic
                         polypeptide
VARIANT                 1..40
                        note = This sequence may encompass 12-40 'G' repeating
                         units wherein some positions may be absent
source                  1..40
                        mol_type = protein
                        organism = synthetic construct
```

-continued

```
SEQUENCE: 5
GGGGGGGGGG GGGGGGGGGG GGGGGGGGGG GGGGGGGGGG                      40

SEQ ID NO: 6            moltype = AA  length = 33
FEATURE                 Location/Qualifiers
REGION                  1..33
                        note = Description of Artificial Sequence: Synthetic
                         polypeptide
VARIANT                 1..33
                        note = This sequence may encompass 1-3 'GGGSGSGGGGS'
                         repeating units wherein some positions may be absent
source                  1..33
                        mol_type = protein
                        organism = synthetic construct
SEQUENCE: 6
GGGSGSGGGG SGGGSGSGGG GSGGGSGSGG GGS                             33

SEQ ID NO: 7            moltype = AA  length = 33
FEATURE                 Location/Qualifiers
REGION                  1..33
                        note = Description of Artificial Sequence: Synthetic
                         polypeptide
VARIANT                 1..33
                        note = This sequence may encompass 1-3 'GGGGGPGGGGP'
                         repeating units wherein some positions may be absent
source                  1..33
                        mol_type = protein
                        organism = synthetic construct
SEQUENCE: 7
GGGGGPGGGG PGGGGGPGGG GPGGGGGPGG GGP                             33

SEQ ID NO: 8            moltype = AA  length = 36
FEATURE                 Location/Qualifiers
REGION                  1..36
                        note = Description of Artificial Sequence: Synthetic
                         polypeptide
VARIANT                 1..36
                        note = This sequence may encompass 2-6 'GGSGGD' repeating
                         units wherein some positions may be absent
source                  1..36
                        mol_type = protein
                        organism = synthetic construct
SEQUENCE: 8
GGSGGDGGSG GDGGSGGDGG SGGDGGSGGD GGSGGD                          36

SEQ ID NO: 9            moltype = AA  length = 36
FEATURE                 Location/Qualifiers
REGION                  1..36
                        note = Description of Artificial Sequence: Synthetic
                         polypeptide
VARIANT                 1..36
                        note = This sequence may encompass 2-6 'GGSGGE' repeating
                         units wherein some positions may be absent
source                  1..36
                        mol_type = protein
                        organism = synthetic construct
SEQUENCE: 9
GGSGGEGGSG GEGGSGGEGG SGGEGGSGGE GGSGGE                          36

SEQ ID NO: 10           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-20 'GS' repeating units
                         wherein some positions may be absent
VARIANT                 41..76
                        note = This region may encompass 2-6 'GGSGGD' repeating
                         units wherein some positions may be absent
VARIANT                 77..116
                        note = This region may encompass 0-20 'GS' repeating units
                         wherein some positions may be absent
source                  1..116
                        mol_type = protein
                        organism = synthetic construct
SEQUENCE: 10
GSGSGSGSGS GSGSGSGSGS GSGSGSGSGS GSGSGSGSGS GGSGGDGGSG GDGGSGGDGG  60
SGGDGGSGGD GGSGGDGSGS GSGSGSGSGS GSGSGSGSGS GSGSGSGSGS GSGSGS      116
```

-continued

```
SEQ ID NO: 11           moltype = AA  length = 114
FEATURE                 Location/Qualifiers
REGION                  1..114
                        note = Description of Artificial Sequence: Synthetic
                         polypeptide
VARIANT                 1..39
                        note = This region may encompass 0-13 'GGS' repeating units
                         wherein some positions may be absent
VARIANT                 40..75
                        note = This region may encompass 2-6 'GGSGGD' repeating
                         units wherein some positions may be absent
VARIANT                 76..114
                        note = This region may encompass 0-13 'GGS' repeating units
                         wherein some positions may be absent
source                  1..114
                        mol_type = protein
                        organism = synthetic construct
SEQUENCE: 11
GGSGGSGGSG GSGGSGGSGG SGGSGGSGGS GGSGGSGGSG GSGGDGGSGG DGGSGGDGGS  60
GGDGGSGGDG GSGGDGGSGG SGGSGGSGGS GGSGGSGGSG GSGGSGGSGG SGGS        114

SEQ ID NO: 12           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-10 'GGGS' repeating
                         units wherein some positions may be absent
VARIANT                 41..76
                        note = This region may encompass 2-6 'GGSGGD' repeating
                         units wherein some positions may be absent
VARIANT                 77..116
                        note = This region may encompass 0-10 'GGGS' repeating
                         units wherein some positions may be absent
source                  1..116
                        mol_type = protein
                        organism = synthetic construct
SEQUENCE: 12
GGGSGGGSGG GSGGGSGGGS GGGSGGGSGG GSGGGSGGGS GGSGGDGGSG GDGGSGGDGG  60
SGGDGGSGGD GGSGGDGGGS GGGSGGGSGG GSGGGSGGGS GGGSGGGSGG GSGGGS      116

SEQ ID NO: 13           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-8 'GGGGS' repeating
                         units wherein some positions may be absent
VARIANT                 41..76
                        note = This region may encompass 2-6 'GGSGGD' repeating
                         units wherein some positions may be absent
VARIANT                 77..116
                        note = This region may encompass 0-8 'GGGGS' repeating
                         units wherein some positions may be absent
source                  1..116
                        mol_type = protein
                        organism = synthetic construct
SEQUENCE: 13
GGGGSGGGGS GGGGSGGGGS GGGGSGGGGS GGGGSGGGGS GGSGGDGGSG GDGGSGGDGG  60
SGGDGGSGGD GGSGGDGGGG SGGGGSGGGG SGGGGSGGGG SGGGGSGGGG SGGGGS      116

SEQ ID NO: 14           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-40 'G' repeating units
                         wherein some positions may be absent
VARIANT                 41..76
                        note = This region may encompass 2-6 'GGSGGD' repeating
                         units wherein some positions may be absent
VARIANT                 77..116
                        note = This region may encompass 0-40 'G' repeating units
                         wherein some positions may be absent
```

-continued

```
source                  1..116
                        mol_type = protein
                        organism = synthetic construct
SEQUENCE: 14
GGGGGGGGGG GGGGGGGGGG GGGGGGGGGG GGGGGGGGGG GGSGGDGGSG GDGGSGGDGG  60
SGGDGGSGGD GGSGGDGGGG GGGGGGGGGG GGGGGGGGGG GGGGGGGGGG GGGGGG      116

SEQ ID NO: 15           moltype = AA  length = 102
FEATURE                 Location/Qualifiers
REGION                  1..102
                        note = Description of Artificial Sequence: Synthetic
                         polypeptide
VARIANT                 1..33
                        note = his region may encompass 0-3 'GGGSGSGGGGS' repeating
                         units wherein some positions may be absent
VARIANT                 34..69
                        note = This region may encompass 2-6 'GGSGGD' repeating
                         units wherein some positions may be absent
VARIANT                 70..102
                        note = This region may encompass 0-3 'GGGSGSGGGGS'
                         repeating units wherein some positions may be absent
source                  1..102
                        mol_type = protein
                        organism = synthetic construct
SEQUENCE: 15
GGGSGSGGGG SGGGSGSGGG GSGGGSGSGG GGSGGSGGDG GSGGDGGSGG DGGSGGDGGS  60
GGDGGSGGDG GGSGSGGGGS GGGSGSGGGG SGGGSGSGGG GS                     102

SEQ ID NO: 16           moltype = AA  length = 102
FEATURE                 Location/Qualifiers
REGION                  1..102
                        note = Description of Artificial Sequence: Synthetic
                         polypeptide
VARIANT                 1..33
                        note = This region may encompass 0-3 'GGGSGSGGGGP'
                         repeating units wherein some positions may be absent
VARIANT                 34..69
                        note = This region may encompass 2-6 'GGSGGD' repeating
                         units wherein some positions may be absent
VARIANT                 70..102
                        note = This region may encompass 0-3 'GGGSGSGGGGP'
                         repeating units wherein some positions may be absent
source                  1..102
                        mol_type = protein
                        organism = synthetic construct
SEQUENCE: 16
GGGSGSGGGG PGGGSGSGGG GPGGGSGSGG GGPGGSGGDG GSGGDGGSGG DGGSGGDGGS  60
GGDGGSGGDG GGSGSGGGGP GGGSGSGGGG PGGGSGSGGG GP                     102

SEQ ID NO: 17           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-20 'GS' repeating units
                         wherein some positions may be absent
VARIANT                 41..76
                        note = This region may encompass 2-6 'GGSGGE' repeating
                         units wherein some positions may be absent
VARIANT                 77..116
                        note = This region may encompass 0-20 'GS' repeating units
                         wherein some positions may be absent
source                  1..116
                        mol_type = protein
                        organism = synthetic construct
SEQUENCE: 17
GSGSGSGSGS GSGSGSGSGS GSGSGSGSGS GSGSGSGSGS GGSGGEGGSG GEGGSGGEGG  60
SGGEGGSGGE GGSGGEGSGS GSGSGSGSGS GSGSGSGSGS GSGSGSGSGS GSGSGS      116

SEQ ID NO: 18           moltype = AA  length = 114
FEATURE                 Location/Qualifiers
REGION                  1..114
                        note = Description of Artificial Sequence: Synthetic
                         polypeptide
VARIANT                 1..39
                        note = This region may encompass 0-13 'GGS' repeating units
                         wherein some positions may be absent
```

-continued

```
VARIANT                 40..75
                        note = This region may encompass 2-6 'GGSGGE' repeating
                         units wherein some positions may be absent
VARIANT                 76..114
                        note = This region may encompass 0-13 'GGS' repeating units
                         wherein some positions may be absent
source                  1..114
                        mol_type = protein
                        organism = synthetic construct
SEQUENCE: 18
GGSGGSGGSG GSGGSGGSGG SGGSGGSGGS GGSGGSGGSG GSGGEGGSGG EGGSGGEGGS  60
GGEGGSGGEG GSGGEGGSGG SGGSGGSGGS GGSGGSGGSG GSGGSGGSGG SGGS        114

SEQ ID NO: 19           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-10 'GGGS' repeating
                         units wherein some positions may be absent
VARIANT                 41..76
                        note = This region may encompass 2-6 'GGSGGE' repeating
                         units wherein some positions may be absent
VARIANT                 77..116
                        note = This region may encompass 0-10 'GGGS' repeating
                         units wherein some positions may be absent
source                  1..116
                        mol_type = protein
                        organism = synthetic construct
SEQUENCE: 19
GGGSGGGSGG GSGGGSGGGS GGGSGGGSGG GSGGGSGGGS GGSGGEGGSG GEGGSGGEGG  60
SGGEGGSGGE GGSGGEGGGS GGGSGGGSGG GSGGGSGGGS GGGSGGGSGG GSGGGS      116

SEQ ID NO: 20           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-8 'GGGGS' repeating
                         units wherein some positions may be absent
VARIANT                 41..76
                        note = This region may encompass 2-6 'GGSGGE' repeating
                         units wherein some positions may be absent
VARIANT                 77..116
                        note = This region may encompass 0-8 'GGGGS' repeating
                         units wherein some positions may be absent
source                  1..116
                        mol_type = protein
                        organism = synthetic construct
SEQUENCE: 20
GGGGSGGGGS GGGGSGGGGS GGGGSGGGGS GGGGSGGGGS GGSGGEGGSG GEGGSGGEGG  60
SGGEGGSGGE GGSGGEGGGG SGGGGSGGGG SGGGGSGGGG SGGGGSGGGG SGGGGS      116

SEQ ID NO: 21           moltype = AA  length = 116
FEATURE                 Location/Qualifiers
REGION                  1..116
                        note = Description of Artificial Sequence: Synthetic
                         polypeptide
VARIANT                 1..40
                        note = This region may encompass 0-40 'G' repeating units
                         wherein some positions may be absent
VARIANT                 41..76
                        note = This region may encompass 2-6 'GGSGGE' repeating
                         units wherein some positions may be absent
VARIANT                 77..116
                        note = This region may encompass 0-40 'G' repeating units
                         wherein some positions may be absent
source                  1..116
                        mol_type = protein
                        organism = synthetic construct
SEQUENCE: 21
GGGGGGGGGG GGGGGGGGGG GGGGGGGGGG GGGGGGGGGG GGSGGEGGSG GEGGSGGEGG  60
SGGEGGSGGE GGSGGEGGGG GGGGGGGGGG GGGGGGGGGG GGGGGGGGGG GGGGGG      116
```

-continued

```
SEQ ID NO: 22           moltype = AA  length = 102
FEATURE                 Location/Qualifiers
REGION                  1..102
                        note = Description of Artificial Sequence: Synthetic
                         polypeptide
VARIANT                 1..33
                        note = This region may encompass 0-3 'GGGSGSGGGGS'
                         repeating units wherein some positions may be absent
VARIANT                 34..69
                        note = This region may encompass 2-6 'GGSGGE' repeating
                         units wherein some positions may be absent
VARIANT                 70..102
                        note = This region may encompass 0-3 'GGGSGSGGGGS'
                         repeating units wherein some positions may be absent
source                  1..102
                        mol_type = protein
                        organism = synthetic construct
SEQUENCE: 22
GGGSGSGGGG SGGGSGSGGG GSGGGSGSGG GGSGGSGGEG GSGGEGGSGG EGGSGGEGGS  60
GGEGGSGGEG GGSGSGGGGS GGGSGSGGGG SGGGSGSGGG GS                     102

SEQ ID NO: 23           moltype = AA  length = 102
FEATURE                 Location/Qualifiers
REGION                  1..102
                        note = Description of Artificial Sequence: Synthetic
                         polypeptide
VARIANT                 1..33
                        note = This region may encompass 0-3 'GGGSGSGGGGP'
                         repeating units wherein some positions may be absent
VARIANT                 34..69
                        note = This region may encompass 2-6 'GGSGGE' repeating
                         units wherein some positions may be absent
VARIANT                 70..102
                        note = This region may encompass 0-3 'GGGSGSGGGGP'
                         repeating units wherein some positions may be absent
source                  1..102
                        mol_type = protein
                        organism = synthetic construct
SEQUENCE: 23
GGGSGSGGGG PGGGSGSGGG GPGGGSGSGG GGPGGSGGEG GSGGEGGSGG EGGSGGEGGS  60
GGEGGSGGEG GGSGSGGGGP GGGSGSGGGG PGGGSGSGGG GP                     102

SEQ ID NO: 24           moltype = AA  length = 40
FEATURE                 Location/Qualifiers
REGION                  1..40
                        note = Description of Artificial Sequence: Synthetic
                         polypeptide
VARIANT                 1..40
                        note = This sequence may encompass at least 20 'GX'
                         repeating units wherein some positions may be absent
VARIANT                 2
                        note = S, D, E, T or P
VARIANT                 4
                        note = S, D, E, T or P
VARIANT                 6
                        note = S, D, E, T or P
VARIANT                 8
                        note = S, D, E, T or P
VARIANT                 10
                        note = S, D, E, T or P
VARIANT                 12
                        note = S, D, E, T or P
VARIANT                 14
                        note = S, D, E, T or P
VARIANT                 16
                        note = S, D, E, T or P
VARIANT                 18
                        note = S, D, E, T or P
VARIANT                 20
                        note = S, D, E, T or P
VARIANT                 22
                        note = S, D, E, T or P
VARIANT                 24
                        note = S, D, E, T or P
VARIANT                 26
                        note = S, D, E, T or P
VARIANT                 28
                        note = S, D, E, T or P
```

-continued

```
VARIANT              30
                     note = S, D, E, T or P
VARIANT              32
                     note = S, D, E, T or P
VARIANT              34
                     note = S, D, E, T or P
VARIANT              36
                     note = S, D, E, T or P
VARIANT              38
                     note = S, D, E, T or P
VARIANT              40
                     note = S, D, E, T or P
source               1..40
                     mol_type = protein
                     organism = synthetic construct
SEQUENCE: 24
GXGXGXGXGX GXGXGXGXGX GXGXGXGXGX GXGXGXGXGX                        40

SEQ ID NO: 25        moltype = AA  length = 39
FEATURE              Location/Qualifiers
REGION               1..39
                     note = Description of Artificial Sequence: Synthetic
                      polypeptide
VARIANT              1..39
                     note = This sequence may encompass at least 13 'GGX'
                      repeating units wherein some positions may be absent
VARIANT              3
                     note = S, D, E, T or P
VARIANT              6
                     note = S, D, E, T or P
VARIANT              9
                     note = S, D, E, T or P
VARIANT              12
                     note = S, D, E, T or P
VARIANT              15
                     note = S, D, E, T or P
VARIANT              18
                     note = S, D, E, T or P
VARIANT              21
                     note = S, D, E, T or P
VARIANT              24
                     note = S, D, E, T or P
VARIANT              27
                     note = S, D, E, T or P
VARIANT              30
                     note = S, D, E, T or P
VARIANT              33
                     note = S, D, E, T or P
VARIANT              36
                     note = S, D, E, T or P
VARIANT              39
                     note = S, D, E, T or P
source               1..39
                     mol_type = protein
                     organism = synthetic construct
SEQUENCE: 25
GGXGGXGGXG GXGGXGGXGG XGGXGGXGGX GGXGGXGGX                         39

SEQ ID NO: 26        moltype = AA  length = 40
FEATURE              Location/Qualifiers
REGION               1..40
                     note = Description of Artificial Sequence: Synthetic
                      polypeptide
VARIANT              1..40
                     note = This sequence may encompass at least 10 'GGGX'
                      repeating units wherein some positions may be absent
VARIANT              4
                     note = S, D, E, T or P
VARIANT              8
                     note = S, D, E, T or P
VARIANT              12
                     note = S, D, E, T or P
VARIANT              16
                     note = S, D, E, T or P
VARIANT              20
                     note = S, D, E, T or P
```

-continued

```
VARIANT                 24
                        note = S, D, E, T or P
VARIANT                 28
                        note = S, D, E, T or P
VARIANT                 32
                        note = S, D, E, T or P
VARIANT                 36
                        note = S, D, E, T or P
VARIANT                 40
                        note = S, D, E, T or P
source                  1..40
                        mol_type = protein
                        organism = synthetic construct
SEQUENCE: 26
GGGXGGGXGG GXGGGXGGGX GGGXGGGXGG GXGGGXGGGX                           40

SEQ ID NO: 27           moltype = AA  length = 40
FEATURE                 Location/Qualifiers
REGION                  1..40
                        note = Description of Artificial Sequence: Synthetic
                         polypeptide
VARIANT                 1..40
                        note = This sequence may encompass at least 8 'GGGGX'
                         repeating units wherein some positions may be absent
VARIANT                 5
                        note = S, D, E, T or P
VARIANT                 10
                        note = S, D, E, T or P
VARIANT                 15
                        note = S, D, E, T or P
VARIANT                 20
                        note = S, D, E, T or P
VARIANT                 25
                        note = S, D, E, T or P
VARIANT                 30
                        note = S, D, E, T or P
VARIANT                 35
                        note = S, D, E, T or P
VARIANT                 40
                        note = S, D, E, T or P
source                  1..40
                        mol_type = protein
                        organism = synthetic construct
SEQUENCE: 27
GGGGXGGGGX GGGGXGGGGX GGGGXGGGGX GGGGXGGGGX                           40

SEQ ID NO: 28           moltype = AA  length = 315
FEATURE                 Location/Qualifiers
REGION                  1..315
                        note = Description of Artificial Sequence: Synthetic
                         polypeptide
VARIANT                 1..315
                        note = This sequence may encompass at least 15 'GZX'
                         repeating units wherein 'Z' is an integer between 1-20 and
                         some positions may be absent
VARIANT                 1..20
                        note = This region may encompass 1-20 'G' repeating units
                         wherein some positions may be absent
VARIANT                 21
                        note = S, D, E, T or P
VARIANT                 22..41
                        note = This region may encompass 1-20 'G' repeating units
                         wherein some positions may be absent
VARIANT                 42
                        note = S, D, E, T or P
VARIANT                 43..62
                        note = This region may encompass 1-20 'G' repeating units
                         wherein some positions may be abent
VARIANT                 63
                        note = S, D, E, T or P
VARIANT                 64..83
                        note = This region may encompass 1-20 'G' repeating units
                         wherein some positions may be absent
VARIANT                 84
VARIANT                 85..104
                        note = This region may encompass 1-20 'G' repeating units
                         wherein some positions may be absent
VARIANT                 105
                        note = S, D, E, T or P
```

-continued

```
VARIANT                 106..125
                        note = This region may encompass 1-20 'G' repeating units
                         wherein some positions may be absent
VARIANT                 126
                        note = S, D, E, T or P
VARIANT                 127..146
                        note = This region may encompass 1-20 'G' repeating units
                         wherein some positions may be absent
VARIANT                 147
                        note = S, D, E, T or P
VARIANT                 148..167
                        note = This region may encompass 1-20 'G' repeating units
                         wherein some positions may be absent
VARIANT                 168
                        note = S, D, E, T or P
VARIANT                 169..188
                        note = This region may encompass 1-20 'G' repeating units
                         wherein some positions may be absent
VARIANT                 189
                        note = S, D, E, T or P
VARIANT                 190..209
                        note = This region may encompass 1-20 'G' repeating units
                         wherein some positions may be abent
VARIANT                 210
                        note = S, D, E, T or P
VARIANT                 211..230
                        note = This region may encompass 1-20 'G' repeating units
                         wherein some positions may be absent
VARIANT                 231
VARIANT                 232..251
                        note = This region may encompass 1-20 'G' repeating units
                         wherein some positions may be absent
VARIANT                 252
                        note = S, D, E, T or P
VARIANT                 253..272
                        note = This region may encompass 1-20 'G' repeating units
                         wherein some positions may be absent
VARIANT                 273
                        note = S, D, E, T or P
VARIANT                 274..293
                        note = This region may encompass 1-20 'G' repeating units
                         wherein some positions may be absent
VARIANT                 294
                        note = S, D, E, T or P
VARIANT                 295..314
                        note = This region may encompass 1-20 'G' repeating units
                         wherein some positions may be absent
VARIANT                 315
                        note = S, D, E, T or P
source                  1..315
                        mol_type = protein
                        organism = synthetic construct
SEQUENCE: 28
GGGGGGGGGG GGGGGGGGGG XGGGGGGGGG GGGGGGGGGG GXGGGGGGGG GGGGGGGGGG  60
GGXGGGGGGG GGGGGGGGGG GGGXGGGGGG GGGGGGGGGG GGGGXGGGGG GGGGGGGGGG  120
GGGGGXGGGG GGGGGGGGGG GGGGGGXGGG GGGGGGGGGG GGGGGGGXGG GGGGGGGGGG  180
GGGGGGGGXG GGGGGGGGGG GGGGGGGGGX GGGGGGGGGG GGGGGGGGGG XGGGGGGGGG  240
GGGGGGGGGG GXGGGGGGGG GGGGGGGGGG GGXGGGGGGG GGGGGGGGGG GGGXGGGGGG  300
GGGGGGGGGG GGGGX                                                   315

SEQ ID NO: 29           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 29
TLDDMSHVIL YA                                                      12

SEQ ID NO: 30           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 30
VISDNHQIVW DL                                                      12
```

```
SEQ ID NO: 31           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 31
LTTQDHPLTI LL                                                     12

SEQ ID NO: 32           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 32
GGWICHWLEP QEACTY                                                 16

SEQ ID NO: 33           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 33
GGCFEEHEQL VFQTHC                                                 16

SEQ ID NO: 34           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 34
GGCILPGQHE SQAIAC                                                 16

SEQ ID NO: 35           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 35
GGCLSQMDFH DWLQYC                                                 16

SEQ ID NO: 36           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 36
GGTDCYLWDY KASCHQ                                                 16

SEQ ID NO: 37           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 37
GGKCDSLSYW QEIECS                                                 16

SEQ ID NO: 38           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
```

-continued

```
SEQUENCE: 38
GGADCLLHDW DSACQI                                          16

SEQ ID NO: 39           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 39
MQNVDEAPPL LL                                              12

SEQ ID NO: 40           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 40
TNDWQGLLLN VF                                              12

SEQ ID NO: 41           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 41
GGCQDSMFHH PNHC                                            14

SEQ ID NO: 42           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 42
GGCGMHQHPL FVDC                                            14

SEQ ID NO: 43           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 43
GGCSLSQHPN HSDC                                            14

SEQ ID NO: 44           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 44
GGPCNQVECH HQFT                                            14

SEQ ID NO: 45           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 45
GGCPSLHPQW IHVC                                            14

SEQ ID NO: 46           moltype = AA  length = 14
FEATURE                 Location/Qualifiers
REGION                  1..14
                        note = Description of Artificial Sequence: Synthetic peptide
```

-continued

```
source                   1..14
                         mol_type = protein
                         organism = synthetic construct
SEQUENCE: 46
GGCFDSANQH PNMC                                                            14

SEQ ID NO: 47            moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 47
GGCHQDIHHP IYWC                                                            14

SEQ ID NO: 48            moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 48
GGCQIHDPHT WHLC                                                            14

SEQ ID NO: 49            moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 49
QLFYPSTYHI ID                                                              12

SEQ ID NO: 50            moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 50
QVSPLYFYEE LA                                                              12

SEQ ID NO: 51            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 51
HQALLDFYGD Y                                                               11

SEQ ID NO: 52            moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 52
GGMCHELFYS NLNWCQ                                                          16

SEQ ID NO: 53            moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 53
GGHCVDMVDF YQQTCQ                                                          16

SEQ ID NO: 54            moltype = AA  length = 12
FEATURE                  Location/Qualifiers
```

-continued

```
REGION                1..12
                      note = Description of Artificial Sequence: Synthetic peptide
source                1..12
                      mol_type = protein
                      organism = synthetic construct
SEQUENCE: 54
VDLLDGSLQD FY                                                           12

SEQ ID NO: 55         moltype = AA  length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 55
GGLCSTFYEP QVDICY                                                       16

SEQ ID NO: 56         moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 56
SDFSGLLFYD YQ                                                           12

SEQ ID NO: 57         moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 57
GGCVHFFHHQ RPDC                                                         14

SEQ ID NO: 58         moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 58
GGCHNKSGLF YHYC                                                         14

SEQ ID NO: 59         moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 59
GGCFYPGHHH QLLC                                                         14

SEQ ID NO: 60         moltype = AA  length = 26
FEATURE               Location/Qualifiers
REGION                1..26
                      note = Description of Artificial Sequence: Synthetic peptide
source                1..26
                      mol_type = protein
                      organism = synthetic construct
SEQUENCE: 60
GSSGGSGGSG GSGGGSGGGS GGSSGT                                            26

SEQ ID NO: 61         moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 61
PCNQVECHHQ FT                                                           12

SEQ ID NO: 62         moltype = AA  length = 219
```

-continued

```
FEATURE                Location/Qualifiers
source                 1..219
                       mol_type = protein
                       organism = Mus sp.
SEQUENCE: 62
DIVMTQTTLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGGGTKLE IKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                         219

SEQ ID NO: 63          moltype = AA  length = 261
FEATURE                Location/Qualifiers
REGION                 1..261
                       note = Description of Artificial Sequence: Synthetic
                        polypeptide
source                 1..261
                       mol_type = protein
                       organism = synthetic construct
SEQUENCE: 63
GGADCLLHDW DSACQIGSSG GSGGSGGSGG GSGGGSGGSS GTDIVMTQTT LSLPVSLGDQ  60
ASISCRSSQS IVHSNGNTYL EWYLQKPGQS PKLLIYKVSN RFSGVPDRFS GSGSGTDFTL  120
KISRVEAEDL GVYYCFQGSH VPYTFGGGTK LEIKRADAAP TVSIFPPSSE QLTSGGASVV  180
CFLNNFYPKD INVKWKIDGS ERQNGVLNSW TDQDSKDSTY SMSSTLTLTK DEYERHNSYT  240
CEATHKTSTS PIVKSFNRNE C                                            261

SEQ ID NO: 64          moltype = AA  length = 259
FEATURE                Location/Qualifiers
REGION                 1..259
                       note = Description of Artificial Sequence: Synthetic
                        polypeptide
source                 1..259
                       mol_type = protein
                       organism = synthetic construct
SEQUENCE: 64
GGCQDSMFHH PNHCGSSGGS GGSGGSGGGS GGGSGGSSGT DIVMTQTTLS LPVSLGDQAS  60
ISCRSSQSIV HSNGNTYLEW YLQKPGQSPK LLIYKVSNRF SGVPDRFSGS GSGTDFTLKI  120
SRVEAEDLGV YYCFQGSHVP YTFGGGTKLE IKRADAAPTV SIFPPSSEQL TSGGASVVCF  180
LNNFYPKDIN VKWKIDGSER QNGVLNSWTD QDSKDSTYSM SSTLTLTKDE YERHNSYTCE  240
ATHKTSTSPI VKSFNRNEC                                               259

SEQ ID NO: 65          moltype = AA  length = 259
FEATURE                Location/Qualifiers
REGION                 1..259
                       note = Description of Artificial Sequence: Synthetic
                        polypeptide
source                 1..259
                       mol_type = protein
                       organism = synthetic construct
SEQUENCE: 65
GGCSLSQHPN HSDCGSSGGS GGSGGSGGGS GGGSGGSSGT DIVMTQTTLS LPVSLGDQAS  60
ISCRSSQSIV HSNGNTYLEW YLQKPGQSPK LLIYKVSNRF SGVPDRFSGS GSGTDFTLKI  120
SRVEAEDLGV YYCFQGSHVP YTFGGGTKLE IKRADAAPTV SIFPPSSEQL TSGGASVVCF  180
LNNFYPKDIN VKWKIDGSER QNGVLNSWTD QDSKDSTYSM SSTLTLTKDE YERHNSYTCE  240
ATHKTSTSPI VKSFNRNEC                                               259

SEQ ID NO: 66          moltype = AA  length = 259
FEATURE                Location/Qualifiers
REGION                 1..259
                       note = Description of Artificial Sequence: Synthetic
                        polypeptide
source                 1..259
                       mol_type = protein
                       organism = synthetic construct
SEQUENCE: 66
GGPCNQVECH HQFTGSSGGS GGSGGSGGGS GGGSGGSSGT DIVMTQTTLS LPVSLGDQAS  60
ISCRSSQSIV HSNGNTYLEW YLQKPGQSPK LLIYKVSNRF SGVPDRFSGS GSGTDFTLKI  120
SRVEAEDLGV YYCFQGSHVP YTFGGGTKLE IKRADAAPTV SIFPPSSEQL TSGGASVVCF  180
LNNFYPKDIN VKWKIDGSER QNGVLNSWTD QDSKDSTYSM SSTLTLTKDE YERHNSYTCE  240
ATHKTSTSPI VKSFNRNEC                                               259

SEQ ID NO: 67          moltype = AA  length = 453
FEATURE                Location/Qualifiers
REGION                 1..453
                       note = Description of Artificial Sequence: Synthetic
                        polypeptide
source                 1..453
                       mol_type = protein
                       organism = synthetic construct
```

-continued

```
SEQUENCE: 67
EAKLQESGPV LVKPGASVKM SCKASGYTFT DYYMNWVKQS HGKSLEWIGV INPYNGDTSY  60
NQKFKGKATL TVDKSSSTAY MELNSLTSED SAVYYCARYY GSWFAYWGQG TLITVSTAKT  120
TPPSVYPLAP GCGDTTGSSV TLGCLVKGYF PESVTVTWNS GSLSSSVHTF PALLQSGLYT  180
MSSSVTVPSS TWPSQTVTCS VAHPASSTTV DKKLEPSGPI STINPCPPCK ECHKCPAPNL  240
EGGPSVFIFP PNIKDVLMIS LTPKVTCVVV DVSEDDPDVR ISWFVNNVEV HTAQTQTHRE  300
DYNSTIRVVS ALPIQHQDWM SGKEFKCKVN NKDLPSPIER TISKIKGLVR APQVYILPPP  360
AEQLSRKDVS LTCLVVGFNP GDISVEWTSN GHTEENYKDT APVLDSDGSY FIYSKLDIKT  420
SKWEKTDSFS CNVRHEGLKN YYLKKTISRS PGK                              453

SEQ ID NO: 68           moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 68
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 69           moltype = AA  length = 256
FEATURE                 Location/Qualifiers
REGION                  1..256
                        note = Description of Artificial Sequence: Synthetic
                         polypeptide
source                  1..256
                        mol_type = protein
                        organism = synthetic construct
SEQUENCE: 69
GGHCVDMVDF YQQTCQGSSG GSGGSGGSGG GSGGGSGGSS GTDIQMTQSP SSLSASVGDR  60
VTITCRASQD VSTAVAWYQQ KPGKAPKLLI YSASFLYSGV PSRFSGSGSG TDFTLTISSL  120
QPEDFATYYC QQYLYHPATF GQGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 70           moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 70
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448
```